(12) United States Patent
Hoves et al.

(10) Patent No.: US 9,890,124 B2
(45) Date of Patent: Feb. 13, 2018

(54) BENZAZEPINE SULFONAMIDE COMPOUNDS

(71) Applicant: Hoffmann-La Roche Inc., Little Falls, NJ (US)

(72) Inventors: Sabine Hoves, Habach (DE); Matthias Koerner, Grenzach-Wyhlen (DE); Lisha Wang, Riehen (CH); Hongying Yun, Shanghai (CN); Wei Zhu, Shanghai (CN); Weixing Zhang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/622,553

(22) Filed: Jun. 14, 2017

(65) Prior Publication Data

US 2017/0275253 A1    Sep. 28, 2017

Related U.S. Application Data

(63) Continuation of application No. PCT/EP2015/079679, filed on Dec. 15, 2015.

(51) Int. Cl.
| | |
|---|---|
| *A61P 35/00* | (2006.01) |
| *C07D 401/12* | (2006.01) |
| *C07D 223/16* | (2006.01) |
| *C07D 401/04* | (2006.01) |
| *C07D 403/12* | (2006.01) |
| *A61P 37/00* | (2006.01) |
| *A61K 31/55* | (2006.01) |
| *C07D 401/14* | (2006.01) |
| *C07D 401/10* | (2006.01) |

(52) U.S. Cl.
CPC ......... *C07D 223/16* (2013.01); *C07D 401/04* (2013.01); *C07D 401/10* (2013.01); *C07D 401/12* (2013.01); *C07D 401/14* (2013.01); *C07D 403/12* (2013.01)

(58) Field of Classification Search
CPC .. C07D 223/16; C07D 401/10; C07D 401/12; C07D 401/14; C07D 403/12
USPC ......................................................... 540/593
See application file for complete search history.

(56) References Cited

U.S. PATENT DOCUMENTS

| | | | | |
|---|---|---|---|---|
| 9,475,775 B2 * | 10/2016 | Hoves | .............. | C07D 223/16 |
| 9,597,333 B2 * | 3/2017 | Hoves | .............. | C07D 223/16 |
| 2008/0234251 A1 * | 9/2008 | Doherty | .............. | C07D 223/16 |
| | | | | 514/213.01 |
| 2010/0029585 A1 * | 2/2010 | Howbert | .............. | A61K 9/0019 |
| | | | | 514/58 |
| 2010/0216989 A1 * | 8/2010 | Howbert | .............. | C07D 223/16 |
| | | | | 540/594 |
| 2011/0092485 A1 * | 4/2011 | Howbert | .............. | C07D 223/14 |
| | | | | 514/213.01 |
| 2011/0118235 A1 * | 5/2011 | Howbert | .............. | A61K 31/4025 |
| | | | | 514/213.01 |
| 2012/0082658 A1 | 4/2012 | Hershberg et al. | | |
| 2014/0088085 A1 * | 3/2014 | Burgess | .............. | C07D 223/16 |
| | | | | 514/214.02 |

FOREIGN PATENT DOCUMENTS

| | | | |
|---|---|---|---|
| WO | 2007/024612 A2 | | 3/2007 |
| WO | WO 2012097173 | * | 7/2012 |
| WO | WO 2017046112 | * | 3/2017 |

OTHER PUBLICATIONS

Holldack; Drug Discovery Today 2014, 19, 379-382. (Year: 2014).*
Hennessy; Nature Reviews: Drug Discovery 2010, 9293-9307. (Year: 2010).*
Lu; Clinical Cancer Research 2012, 18, 499-509. (Year: 2012).*
Stephenson;Cancer Immunol Immunother 2013, 62, 1347-1357. (Year: 2013).*
Dietsch; Clinical Cancer Research 2015, 21, 5445-5452. (Year: 2015).*
Brueseke; Clinical Pharmacology: Advances and Applications 2013, 5 (Suppl 1), 13-19. (Year: 2013).*
ISR and Written Opinion for PCT/EP2015/079679 (dated Mar. 8, 2016).

* cited by examiner

*Primary Examiner* — Daniel R Carcanague
(74) *Attorney, Agent, or Firm* — Brian L. Buckwalter

(57) ABSTRACT

This invention relates to novel benzazepine sulfonamide compounds of the formula

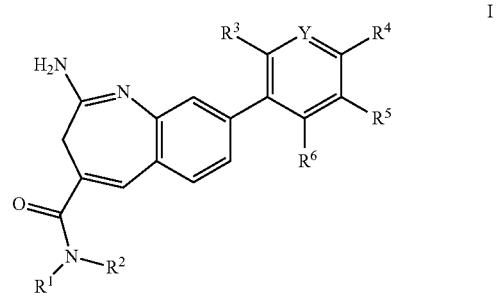

wherein $R^4$ or $R^5$ is —$SO_2$—$NR^7R^8$ and $R^1$ to $R^8$ and Y are as defined in the description and in the claims, as well as pharmaceutically acceptable salts thereof. These compounds are TLR agonists and may therefore be useful as medicaments for the treatment of diseases such as cancer, autoimmune diseases, inflammation, sepsis, allergy, asthma, graft rejection, graft-versus-host disease, immunodeficiencies, and infectious diseases.

20 Claims, No Drawings

BENZAZEPINE SULFONAMIDE COMPOUNDS

CROSS REFERENCE TO RELATED APPLICATIONS

This application is a continuation of PCT/EP2015/079679 having an international filing date of Dec. 15, 2015 and which claims benefit under 35 U.S.C. § 119 to PCT/CN2014/094181 having an international filing date of Dec. 18, 2014. The entire contents of both applications are hereby incorporated by reference in their entirety.

FIELD OF THE INVENTION

The present invention relates to novel benzazepine sulfonamide compounds having pharmaceutical activity, their manufacture, pharmaceutical compositions containing them and their potential use as medicaments.

BACKGROUND OF THE INVENTION

The compounds of formula I are TLR agonists. More particularly, the compounds are TLR8 agonists and may be useful for the treatment and prevention (e.g. vaccination) of cancer, autoimmune diseases, inflammation, sepsis, allergy, asthma, graft rejection, graft-versus-host disease, immunodeficiencies, and infectious diseases.

Toll-like receptors (TLRs) are a family of membrane-spanning receptors that are expressed on cells of the immune system like dendritic cells, macrophages, monocytes, T cells, B cells, NK cells and mast cells but also on a variety of non-immune cells such as endothelial cells, epithelial cells and even tumor cells (Kawai et al., Immunity, 2011, 34, 637-650, Kawai et al., Nat. Immunol., 2010, 11, 373-384). TLRs that recognize bacterial and fungal components are expressed on the cell surface (i.e. TLR1, 2, 4, 5 and 6), while others that recognize viral or microbial nucleic acids like TLR3, 7, 8 and 9 are localized to the endolysosomal/phagosomal compartment (Henessy et al. Nat. Rev. Drug Discovery 2010, 9, 293-307) and predominantly found to be expressed by cells of the myeloid lineage. TLR ligation leads to activation of NF-κB and IRF-dependent pathways with the specific activation sequence and response with respect to the specific TLR and cell type. While TLR7 is mainly expressed in all dendritic cells subtypes (DC and here highly in pDC, plasmacytoid DC) and can be induced in B cells upon IFNα stimulation (Bekeredjian-Ding et al. J. Immunology 2005, 174:4043-4050), TLR8 expression is rather restricted to monocytes, macrophages and myeloid DC. TLR8 signaling via MyD88 can be activated by bacterial single stranded RNA, small molecule agonists and lately discovered microRNAs (Chen et al. RNA 2013, 19:737-739). The activation of TLR8 results in the production of various pro-inflammatory cytokines such as IL-6, IL-12 and TNF-α as well as enhanced expression of co-stimulatory molecules, such as CD80, CD86, and chemokine receptors (Cros et al. Immunity 2010, 33:375-386). In addition, TLR8 activation can induce type I interferon (IFNβ) in primary human monocytes (Pang et al. BMC Immunology 2011, 12:55).

Small molecule agonists for both the TLR7 and TLR8 receptor as well as analogs modified for use as vaccine adjuvants or conjugates have been identified in many patents (i.e. WO1992015582, WO2007024612, WO2009111337, WO2010093436, WO2011017611, WO2011068233, WO2011139348, WO2012066336, WO2012167081, WO2013033345, WO2013166110, and US2013202629). Clinical experience has been obtained mainly for TLR7 agonists, but only very few clinical studies focused on using highly specific TLR8 agonists. To date, the only FDA (U.S. Food and Drug Administration)-approved small molecule drug is the TLR7 agonist imiquimod (ALDARA™) as a topical agent for the treatment of genital warts, superficial basal cell carcinoma and actinic keratosis. Systemic application however of the early TLR7 agonists like resiquimod has been abandoned due to intolerable cardiotoxicity observed upon global chemokine stimulation at therapeutic levels (Holldack, Drug Discovery Today, 2013, 1-4). Knowledge about TLR8 agonists is less advanced and mostly restricted to data with early mixed TLR7/8 agonists like resiquimod. For the resiquimod agonist, however, the stimulatory capacity of the TLR7 is superior compared to the activation of the TLR8, so that most of the effects of resiquimod are dominated by the effect of TLR7 activity. More recently, TLR8 specific compounds like VTX-2337 have been described by VentiRX Pharmaceuticals (i.e. WO 2007024612), allowing for the first time to analyse the specific role of TLR8 without activation of TLR7 at the same time.

SUMMARY OF THE INVENTION

The present invention relates to benzazepine-4-carboxamide compounds of the formula (I)

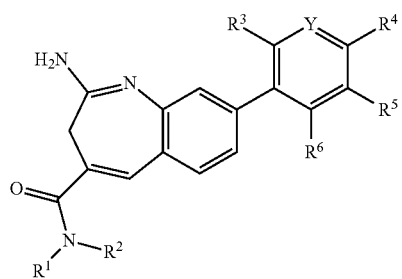

wherein
$R^1$ and $R^2$ are the same or different and are selected from the group consisting of $C_{1-7}$-alkyl, hydroxy-$C_{2-7}$-alkyl, $C_{2-7}$-alkenyl and $C_{3-7}$-alkynyl;
$R^3$ is hydrogen or $C_{1-7}$-alkyl;
$R^6$ is hydrogen or $C_{1-7}$-alkyl;
one of $R^4$ and $R^5$ is selected from the group consisting of hydrogen, $C_{1-7}$-alkyl, halogen-$C_{1-7}$-alkyl and $C_{1-7}$-alkoxy,
and the other one of $R^4$ and $R^5$ is —$S(O)_2NR^7R^8$,
wherein $R^7$ and $R^8$ are the same or different and are selected from the group consisting of hydrogen, $C_{1-7}$-alkyl, halogen-$C_{1-7}$-alkyl, hydroxy-$C_{1-7}$-alkyl, hydroxy-$C_{1-7}$-alkoxy-$C_{1-7}$-alkyl, amino-$C_{1-7}$-alkyl, $C_{1-7}$-alkyl-amino-$C_{1-7}$-alkyl, amino-$C_{1-7}$-alkoxy-$C_{1-7}$-alkyl, $C_{1-7}$-alkyl-amino-$C_{1-7}$-alkoxy-$C_{1-7}$-alkyl, amino-$C_{1-7}$-alkyl-carbonyl and $C_{1-7}$-alkyl-amino-$C_{1-7}$-alkyl-carbonyl, or
$R^7$ and $R^8$ together with the nitrogen atom they are attached to form a 4- to 6-membered heterocycle which is unsubstituted or substituted with a group selected from the group consisting of amino, $C_{1-7}$-alkyl-amino, hydroxy and hydroxy-$C_{1-7}$-alkyl and which may contain an additional N—$R^{10}$ group, wherein $R^{10}$ is selected from the group consisting of hydrogen, amino-$C_{1-7}$-alkyl and $C_{1-7}$-alkyl-amino-$C_{1-7}$-alkyl;

Y is N or $CR^9$, wherein $R^9$ is selected from the group consisting of hydrogen, $C_{1-7}$-alkyl and halogen-$C_{1-7}$-alkyl;

or its pharmaceutically acceptable salts.

The invention is also concerned with processes for the manufacture of compounds of formula I.

The invention also relates to pharmaceutical compositions comprising a compound of formula I as described above and a pharmaceutically acceptable carrier and/or adjuvant.

A further aspect of the invention is the use of compounds of formula I as therapeutic active substances for the treatment of diseases that can be mediated with TLR agonists, in particular TLR8 agonists. The invention thus relates to a method for the treatment of a disease that can be mediated with TLR agonists such as for example cancer and autoimmune or infectious diseases.

DETAILED DESCRIPTION OF THE INVENTION

At present there is still a need for small molecule TLR8 agonists, specifically those with improved potency or selectivity.

The present invention is directed to benzazepines with improved cellular potency over known TLR8 agonists of this type for use in the treatment of cancer, preferably solid tumors and lymphomas, and for other uses including the treatment of certain skin conditions or diseases, such as atopic dermatitis, the treatment of infectious diseases, preferably viral diseases, and for use as adjuvants in vaccines formulated for use in cancer therapy or by desensitizing of the receptors by continuous stimulation in the treatment of autoimmune diseases.

Of note, these new compounds have improved cellular potency at TLR8 compared to known TLR8 agonists such as VTX-2337. In addition these compounds are highly specific towards TLR8 and possess only low or even no activity towards TLR7. Thus, they are expected to possess advantageous properties compared to combined TLR7/8 agonists due to the more restricted expression pattern of TLR8 resulting in less served side effects when administered systemically.

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "compound(s) of this invention" and "compound(s) of the present invention" refers to compounds of formula I and solvates or salts thereof (e.g., pharmaceutically acceptable salts).

The term "substituent" denotes an atom or a group of atoms replacing a hydrogen atom on the parent molecule.

The term "halogen" refers to fluoro, chloro, bromo and iodo, with fluoro, chloro and bromo being of particular interest. More particularly, halogen refers to fluoro.

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms. More particularly, the term "alkyl" also embraces lower alkyl groups as described below.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl and ethyl. The term "$C_{2-7}$-alkyl" refers to a straight-chain or branched-chain alkyl group with 2 to 7 carbon atoms as defined above, however the methyl or methylene group is excluded.

The term "lower alkenyl" or "$C_{2-7}$-alkenyl" signifies a straight-chain or branched chain hydrocarbon residue comprising an olefinic bond and 2 to 7, preferably 3 to 6, particularly preferred 3 to 4 carbon atoms. Examples of alkenyl groups are ethenyl, 1-propenyl, 2-propenyl, isopropenyl, 1-butenyl, 2-butenyl, 3-butenyl and isobutenyl, in particular 2-propenyl (allyl).

The term "lower alkinyl" or "$C_{2-7}$-alkinyl" signifies a straight-chain or branched chain hydrocarbon residue comprising a triple bond and 2 to 7 carbon atoms. Examples of lower alkinyl groups are ethinyl and 1-propinyl (—C≡C—$CH_2$).

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl, 2-methoxyethyl and 2-ethoxyethyl, with 2-ethoxyethyl being of most particular interest.

The term hydroxy or hydroxyl means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "lower hydroxyalkoxyalkyl" or "hydroxy-$C_{1-7}$-alkoxy-$C_{1-7}$-alkyl" refers to lower alkoxyalkyl groups as defined above wherein at least one of the hydrogen atoms of the lower alkoxy group is replaced by a hydroxy group. Among the lower hydroxyalkoxyalkyl groups of particular interest is 2-hydroxyethoxyethyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl being of more particular interest.

The term "lower alkylcarbonyl" or "$C_{1-7}$-alkylcarbonyl" means the group —C(O)—R, wherein R is a lower alkyl group as defined above. A lower alkylcarbonyl group of particular interest is methylcarbonyl or acetyl.

"Amino" refers to the group —NH$_2$. The term "C$_{1-7}$-alkylamino" means a group 13 NHR, wherein R is lower alkyl and the term "lower alkyl" has the previously given significance. The term "di-C$_{1-7}$-alkylamino" means a group —NRR', wherein R and R' are lower alkyl groups as defined above.

The term "lower aminoalkyl" or "amino-C$_{1-7}$-alkyl" refers to lower alkyl groups as defined above wherein at least one of the hydrogen atoms of the lower alkyl group is replaced by an amino group. Among the particular interesting lower aminoalkyl groups are aminomethyl or 2-aminoethyl.

The term "lower alkylaminoalkyl" or "C$_{1-7}$-alkylamino-C$_{1-7}$-alkyl" refers to lower alkyl groups as defined above wherein at least one of the hydrogen atoms of the lower alkyl group is replaced by an C$_{1-7}$-alkylamino group. Among the particular interesting lower alkylaminoalkyl groups are ethylaminomethyl or 2-ethylaminoethyl.

The term "lower aminoalkoxyalkyl" or "amino-C$_{1-7}$-alkoxy-C$_{1-7}$-alkyl" refers to lower alkoxyalkyl groups as defined above wherein at least one of the hydrogen atoms of the lower alkoxy group is replaced by an amino group. Among the particular interesting lower aminoalkoxyalkyl groups are 2-aminoethoxymethyl or 2-aminoethoxyethyl.

The term "lower alkylamino-alkoxy-alkyl" or "C$_{1-7}$-alkylamino-C$_{1-7}$-alkoxy-C$_{1-7}$-alkyl" refers to lower alkoxyalkyl groups as defined above wherein at least one of the hydrogen atoms of the lower alkoxy group is replaced by an alkylamino group. Among the particular interesting lower alkylaminoalkoxyalkyl groups are 2-methylaminoethoxymethyl or 2-methylaminoethoxyethyl.

The term "lower aminoalkylcarbonyl" or "amino-C$_{1-7}$-alkylcarbonyl" means the group —C(O)—R, wherein R is a lower aminoalkyl group as defined above. A lower aminoalkylcarbonyl group of particular interest is 2-aminoacetyl.

The term "lower alkylaminoalkylcarbonyl" or "C$_{1-7}$-alkyl-amino-C$_{1-7}$-alkylcarbonyl" means the group —C(O)—R, wherein R is a lower alkylaminoalkyl group as defined above. A lower alkylaminoalkylcarbonyl group of particular interest is 2-ethylaminoacetyl.

The term "heteroaryl" in general refers to an aromatic 5- or 6-membered ring which comprises one, two, three or four atoms selected from nitrogen, oxygen and/or sulfur, such as for example pyridyl. The term "heteroaryl" further refers to bicyclic aromatic groups comprising from 5 to 12 ring atoms, in which one or both rings can contain one, two or three atoms selected from nitrogen, oxygen or sulfur.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

In detail, the present invention relates to compounds of the formula

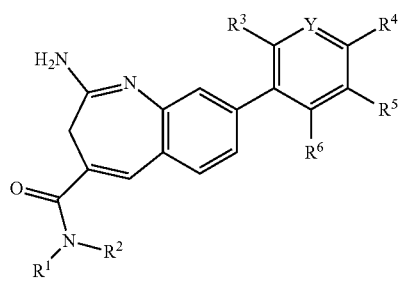

wherein
R$^1$ and R$^2$ are the same or different and are selected from the group consisting of C$_{1-7}$-alkyl, hydroxy-C$_{2-7}$-alkyl, amino-C$_{2-7}$-alkyl, C$_{2-7}$-alkenyl and C$_{3-7}$-alkynyl;

$R^3$ is hydrogen or $C_{1-7}$-alkyl;
$R^6$ is hydrogen or $C_{1-7}$-alkyl;
one of $R^4$ and $R^5$ is selected from the group consisting of hydrogen, $C_{1-7}$-alkyl, halogen-$C_{1-7}$-alkyl and $C_{1-7}$-alkoxy,
and the other one of $R^4$ and $R^5$ is

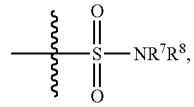

wherein $R^7$ and $R^8$ are the same or different and are selected from the group consisting of hydrogen, $C_{1-7}$-alkyl, halogen-$C_{1-7}$-alkyl, hydroxy-$C_{1-7}$-alkyl, hydroxy-$C_{1-7}$-alkoxy-$C_{1-7}$-alkyl, amino-$C_{1-7}$-alkyl, $C_{1-7}$-alkyl-amino-$C_{1-7}$-alkyl, amino-$C_{1-7}$-alkoxy-$C_{1-7}$-alkyl, $C_{1-7}$-alkyl-amino-$C_{1-7}$-alkoxy-$C_{1-7}$-alkyl, amino-$C_{1-7}$-alkyl-carbonyl and $C_{1-7}$-alkyl-amino-$C_{1-7}$-alkyl-carbonyl, or
$R^7$ and $R^8$ together with the nitrogen atom they are attached to form a 4- to 6-membered heterocycle which is unsubstituted or substituted with a group selected from the group consisting of amino, $C_{1-7}$-alkyl-amino, hydroxy and hydroxy-$C_{1-7}$-alkyl and which may contain an additional N—$R^{10}$ group, wherein $R^{10}$ is selected from the group consisting of hydrogen, amino-$C_{1-7}$-alkyl and $C_{1-7}$-alkyl-amino-$C_{1-7}$-alkyl;
Y is N or $CR^9$,
wherein $R^9$ is selected from the group consisting of hydrogen, $C_{1-7}$-alkyl and halogen-$C_{1-7}$-alkyl;
or its pharmaceutically acceptable salts.

In one aspect, the invention relates to compounds of formula I, wherein $R^1$ is $C_{1-7}$-alkyl.

In particular, the invention is concerned with compounds of formula I, wherein $R^1$ is propyl.

In another aspect, the invention refers to compounds of formula I, wherein $R^2$ is $C_{1-7}$-alkyl.

In one aspect, the invention relates to compounds of formula I, wherein $R^1$ and $R^2$ are $C_{1-7}$-alkyl, in particular propyl.

In a further aspect, the invention relates to compounds of formula I, wherein $R^3$ and $R^6$ are hydrogen.

In one aspect, the invention relates to compounds of formula I, wherein $R^6$ is $C_{1-7}$-alkyl, in particular methyl.

In another aspect, the invention refers to compounds of formula I, wherein $R^4$ is selected from the group consisting of hydrogen, $C_{1-7}$-alkyl, halogen-$C_{1-7}$-alkyl and $C_{1-7}$-alkoxy and $R^5$ is —$S(O)_2NR^7R^8$,
wherein $R^7$ and $R^8$ are the same or different and are selected from the group consisting of hydrogen, $C_{1-7}$-alkyl, halogen-$C_{1-7}$-alkyl, hydroxy-$C_{1-7}$-alkyl, hydroxy-$C_{1-7}$-alkoxy-$C_{1-7}$-alkyl, amino-$C_{1-7}$-alkyl, $C_{1-7}$-alkyl-amino-$C_{1-7}$-alkyl, amino-$C_{1-7}$-alkoxy-$C_{1-7}$-alkyl, $C_{1-7}$-alkyl-amino-$C_{1-7}$-alkoxy-$C_{1-7}$-alkyl, amino-$C_{1-7}$-alkyl-carbonyl and $C_{1-7}$-alkyl-amino-$C_{1-7}$-alkyl-carbonyl, or
$R^7$ and $R^8$ together with the nitrogen atom they are attached to form a 4- to 6-membered heterocycle which is unsubstituted or substituted with a group selected from the group consisting of amino, $C_{1-7}$-alkyl-amino, hydroxy and hydroxy-$C_{1-7}$-alkyl and which may contain an additional N—$R^{10}$ group, wherein $R^{10}$ is selected from the group consisting of hydrogen, amino-$C_{1-7}$-alkyl and $C_{1-7}$-alkyl-amino-$C_{1-7}$-alkyl.

These are the compounds of the formula Ia:

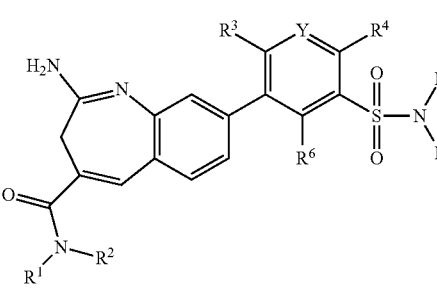

In a further aspect, the invention refers to compounds of formula I, wherein $R^5$ is selected from the group consisting of hydrogen, $C_{1-7}$-alkyl, halogen-$C_{1-7}$-alkyl and $C_{1-7}$-alkoxy and $R^4$ is —$S(O)_2NR^7R^8$
wherein $R^7$ and $R^8$ are the same or different and are selected from the group consisting of hydrogen, $C_{1-7}$-alkyl, halogen-$C_{1-7}$-alkyl, hydroxy-$C_{1-7}$-alkyl, hydroxy-$C_{1-7}$-alkoxy-$C_{1-7}$-alkyl, amino-$C_{1-7}$-alkyl, $C_{1-7}$-alkyl-amino-$C_{1-7}$-alkyl, amino-$C_{1-7}$-alkoxy-$C_{1-7}$-alkyl, $C_{1-7}$-alkyl-amino-$C_{1-7}$-alkoxy-$C_{1-7}$-alkyl, amino-$C_{1-7}$-alkyl-carbonyl and $C_{1-7}$-alkyl-amino-$C_{1-7}$-alkyl-carbonyl, or
$R^7$ and $R^8$ together with the nitrogen atom they are attached to form a 4- to 6-membered heterocycle which is unsubstituted or substituted with a group selected from the group consisting of amino, $C_{1-7}$-alkyl-amino, hydroxy and hydroxy-$C_{1-7}$-alkyl and which may contain an additional N—$R^{10}$ group, wherein $R^{10}$ is selected from the group consisting of hydrogen, amino-$C_{1-7}$-alkyl and $C_{1-7}$-alkyl-amino-$C_{1-7}$-alkyl.

These are the compounds of the formula Ib:

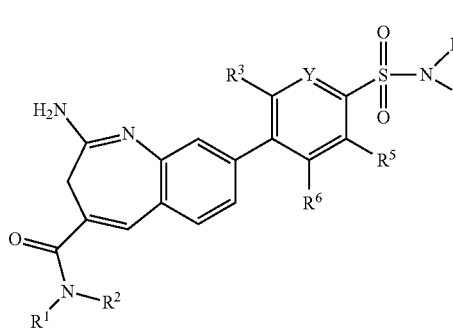

In one aspect, the invention relates to compounds of formula I, wherein $R^7$ and $R^8$ are the same or different and are selected from the group consisting of hydrogen, $C_{1-7}$-alkyl, halogen-$C_{1-7}$-alkyl, hydroxy-$C_{1-7}$-alkyl, hydroxy-$C_{1-7}$-alkoxy-$C_{1-7}$-alkyl, amino-$C_{1-7}$-alkyl, $C_{1-7}$-alkyl-amino-$C_{1-7}$-alkyl, amino-$C_{1-7}$-alkoxy-$C_{1-7}$-alkyl, $C_{1-7}$-alkyl-amino-$C_{1-7}$-alkoxy-$C_{1-7}$-alkyl, amino-$C_{1-7}$-alkyl-carbonyl and $C_{1-7}$-alkyl-amino-$C_{1-7}$-alkyl-carbonyl.

In particular, the invention refers to compounds of formula I, wherein $R^7$ and $R^8$ are the same or different and are selected from the group consisting of hydrogen, $C_{1-7}$-alkyl, hydroxy-$C_{1-7}$-alkyl and hydroxy-$C_{1-7}$-alkoxy-$C_{1-7}$-alkyl.

In another aspect, the invention relates to compounds of formula I, wherein $R^7$ and $R^8$ together with the nitrogen atom they are attached to form a 4- to 6-membered heterocycle which is unsubstituted or substituted with a group selected from the group consisting of amino, $C_{1-7}$-alkyl-amino, hydroxy and hydroxy-$C_{1-7}$-alkyl and which may contain an additional N—$R^{10}$ group, wherein $R^{10}$ is selected from the group consisting of hydrogen, amino-$C_{1-7}$-alkyl and $C_{1-7}$-alkyl-amino-$C_{1-7}$-alkyl.

In a particular aspect, the invention refers to compounds of formula I, wherein $R^7$ and $R^8$ together with the nitrogen atom they are attached to form a 4- to 6-membered heterocycle which is substituted with a group selected from the group consisting of amino, hydroxy and hydroxy-$C_{1-7}$-alkyl.

In particular, the invention is concerned with compounds of formula I, wherein $R^7$ and $R^8$ together with the nitrogen atom they are attached to form a 4- to 6-membered heterocycle which is substituted with a group selected from the group consisting of hydroxy and hydroxy-$C_{1-7}$-alkyl.

In another aspect, the invention relates to compounds of formula I, wherein $R^7$ and $R^8$ together with the nitrogen atom they are attached to form a 5-membered heterocycle which is unsubstituted or substituted with a group selected from the group consisting of amino, hydroxy and hydroxy-$C_{1-7}$-alkyl.

The invention further relates to compounds of formula I, wherein Y is N, meaning compounds of the formula I-c.

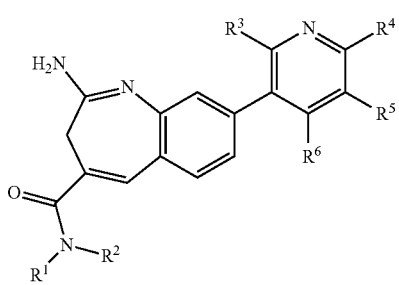

I-c

In a further aspect, the invention relates to compounds of formula I, wherein Y is $CR^9$, and wherein $R^9$ is selected from the group consisting of hydrogen, $C_{1-7}$-alkyl and halogen-$C_{1-7}$-alkyl. These are the compounds of the formula I-d.

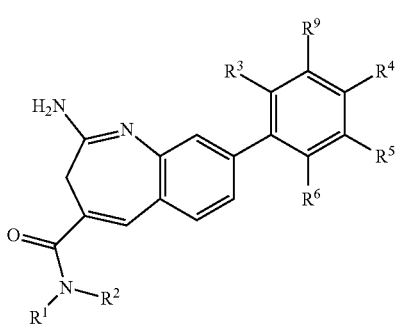

I-d

Particular compounds of formula I according to the invention are the following:
2-amino-N,N-dipropyl-8-(3-sulfamoylphenyl)-3H-1-benzazepine-4-carboxamide,
2-amino-8-[3-(2-hydroxyethylsulfamoyl)phenyl]-N,N-dipropyl-3H-1-benzazepine-4-carboxamide,
2-amino-N,N-dipropyl-8-(3-pyrrolidin-1-ylsulfonylphenyl)-3H-1-benzazepine-4-carboxamide,
2-amino-N,N-dipropyl-8-(5-sulfamoyl-3-pyridyl)-3H-1-benzazepine-4-carboxamide,
2-amino-8-[3-(3-hydroxypyrrolidin-1-yl)sulfonylphenyl]-N,N-dipropyl-3H-1-benzazepine-4-carboxamide,
2-amino-8-[4-(3-hydroxypyrrolidin-1-yl)sulfonylphenyl]-N,N-dipropyl-3H-1-benzazepine-4-carboxamide,
2-amino-8-[3-[(3R)-3-hydroxypyrrolidin-1-yl]sulfonylphenyl]-N,N-dipropyl-3H-1-benzazepine-4-carboxamide,
2-amino-8-[3-[(3S)-3-hydroxypyrrolidin-1-yl]sulfonylphenyl]-N,N-dipropyl-3H-1-benzazepine-4-carboxamide,
2-amino-8-[3-(3-hydroxyazetidin-1-yl)sulfonylphenyl]-N,N-dipropyl-3H-1-benzazepine-4-carboxamide,
2-amino-8-[3-[2-hydroxyethyl(methyl)sulfamoyl]phenyl]-N,N-dipropyl-3H-1-benzazepine-4-carboxamide,
2-amino-8-[3-[2-(2-hydroxyethoxy)ethylsulfamoyl]phenyl]-N,N-dipropyl-3H-1-benzazepine-4-carboxamide,
2-amino-8-[3-(6-hydroxyhexylsulfamoyl)phenyl]-N,N-dipropyl-3H-1-benzazepine-4-carboxamide,
2-amino-8-[3-[(4-hydroxy-1-piperidyl)sulfonyl]phenyl]-N,N-dipropyl-3H-1-benzazepine-4-carboxamide,
2-amino-8-[3-[(3R)-3-hydroxypyrrolidin-1-yl]sulfonyl-5-(trifluoromethyl)phenyl]-N,N-dipropyl-3H-1-benzazepine-4-carboxamide,
2-amino-8-[3-[(3R)-3-hydroxypyrrolidin-1-yl]sulfonyl-4-methoxy-phenyl]-N,N-dipropyl-3H-1-benzazepine-4-carboxamide,
2-amino-8-[3-[3-(hydroxymethyl)azetidin-1-yl]sulfonylphenyl]-N,N-dipropyl-3H-1-benzazepine-4-carboxamide,
2-Amino-8-[3-[[(3R)-3-hydroxy-1-piperidyl]sulfonyl]phenyl]-N,N-dipropyl-3H-1-benzazepine-4-carboxamide,
2-Amino-8-[3-[[(3S)-3-hydroxy-1-piperidyl]sulfonyl]phenyl]-N,N-dipropyl-3H-1-benzazepine-4-carboxamide,
2-Amino-8-[3-[(3R)-3-hydroxypyrrolidin-1-yl]sulfonyl-2-methyl-phenyl]-N,N-dipropyl-3H-1-benzazepine-4-carboxamide,
2-amino-8-(5-piperazin-1-ylsulfonyl-3-pyridyl)-N,N-dipropyl-3H-1-benzazepine-4-carboxamide,
2-amino-8-(3-piperazin-1-ylsulfonylphenyl)-N,N-dipropyl-3H-1-benzazepine-4-carboxamide,
2-amino-8-[5-(3-aminopyrrolidin-1-yl)sulfonyl-3-pyridyl]-N,N-dipropyl-3H-1-benzazepine-4-carboxamide,
2-amino-8-[3-[(3R)-3-hydroxypyrrolidin-1-yl]sulfonyl-5-methyl-phenyl]-N,N-dipropyl-3H-1-benzazepine-4-carboxamide,
and pharmaceutically acceptable salts thereof.

More particularly, the invention relates to the following compounds of formula I:
2-amino-N,N-dipropyl-8-(3-pyrrolidin-1-ylsulfonylphenyl)-3H-1-benzazepine-4-carboxamide,
2-amino-8-[3-(3-hydroxypyrrolidin-1-yl)sulfonylphenyl]-N,N-dipropyl-3H-1-benzazepine-4-carboxamide,
2-amino-8-[4-(3-hydroxypyrrolidin-1-yl)sulfonylphenyl]-N,N-dipropyl-3H-1-benzazepine-4-carboxamide,
2-amino-8-[3-[(3R)-3-hydroxypyrrolidin-1-yl]sulfonyl-5-(trifluoromethyl)phenyl]-N,N-dipropyl-3H-1-benzazepine-4-carboxamide,
2-amino-8-[3-[[(3R)-3-hydroxy-1-piperidyl]sulfonyl]phenyl]-N,N-dipropyl-3H-1-benzazepine-4-carboxamide,
2-amino-8-[3-[[(3S)-3-hydroxy-1-piperidyl]sulfonyl]phenyl]-N,N-dipropyl-3H-1-benzazepine-4-carboxamide,
2-amino-8-(3-piperazin-1-ylsulfonylphenyl)-N,N-dipropyl-3H-1-benzazepine-4-carboxamide,
and pharmaceutically acceptable salts thereof.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) coupling a compound of the formula II

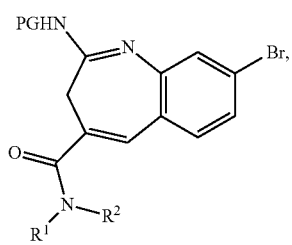

II wherein $R^1$ and $R^2$ are as defined herein before and PG is a protecting group, with a compound of the formula III

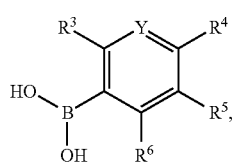

III wherein $R^3$ to $R^6$ and Y are as defined herein before, under basic conditions in the presence of a Pd catalyst and removing the protecting group PG under acidic conditions to obtain a compound of the formula I

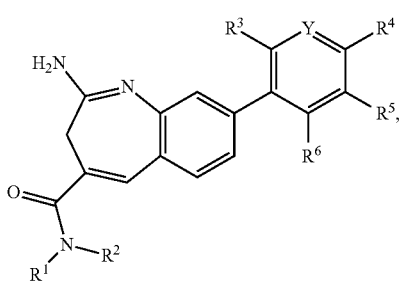

I wherein $R^1$ to $R^6$ and Y are as defined herein before, and, if desired, converting the compound obtained into a pharmaceutically acceptable salt, or b) reacting a compound of the formula II

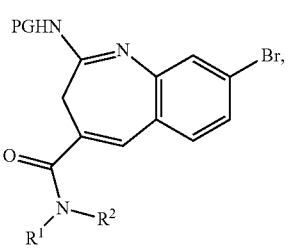

II wherein $R^1$ and $R^2$ are as defined herein before and PG is a protecting group, with bis(pinacolato)diboron under basic conditions in the presence of a Pd catalyst to obtain a boronic ester of the formula V

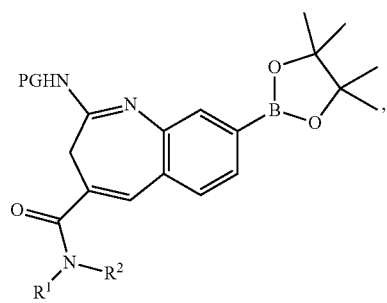

V wherein $R^1$ and $R^2$ are as defined herein before and PG is a protecting group, and coupling the compound V under basic conditions in the presence of a Pd catalyst with a bromide of the formula

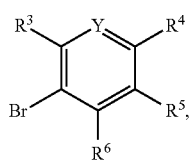

VI wherein $R^3$ to $R^6$ and Y are as defined herein before, and removing the protecting group PG under acidic conditions to obtain a compound of the formula I

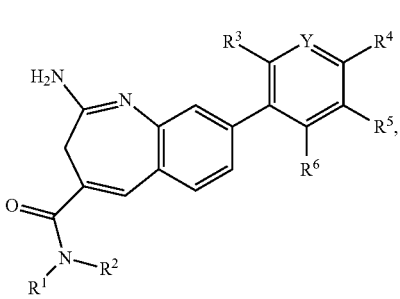

I wherein $R^1$ to $R^6$ and Y are as defined herein before, and, if desired, converting the compound obtained into a pharmaceutically acceptable salt.

In particular, a suitable protecting group PG is an amino-protecting group selected from Boc (tert-butoxycarbonyl), benzyl (Bz) and benzyloxycarbonyl (Cbz). In particular, the protecting group is Boc.

"Removing the protecting group PG under acidic conditions" means treating the protected compound with acids in a suitable solvent, for instance trifluoroacetic acid (TFA) in a solvent such as dichloromethane (DCM) can be employed.

Under basic conditions means the presence of a base, in particular a base selected from the group consisting of sodium carbonate, potassium carbonate, caesium carbonate, potassium phosphate and sodium hydroxide. Typical solvents are selected from the group consisting of 1.4-dioxane, toluene, THF, dimethylformamide and mixtures of water and organic solvents.

The term "Pd catalyst" refers to any Pd(O) catalyst that is appropriate to be used in a Suzuki coupling. Examples for a Pd catalyst appropriate for the Suzuki coupling are selected from the group consisting of $Pd(PPh_3)_4$, $PdCl_2(PPh_3)_2$ and $Pd(dppf)_2Cl_2$.

The invention further relates to compounds of formula I as defined above obtainable according to a process as defined above.

The compounds of the present invention can be prepared by any conventional means. Suitable processes for synthesizing these compounds as well as their starting materials are provided in the schemes below and in the examples. All substituents, in particular, $R^1$ to $R^6$ and Y are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compounds of formula I is shown in Scheme 1 below.

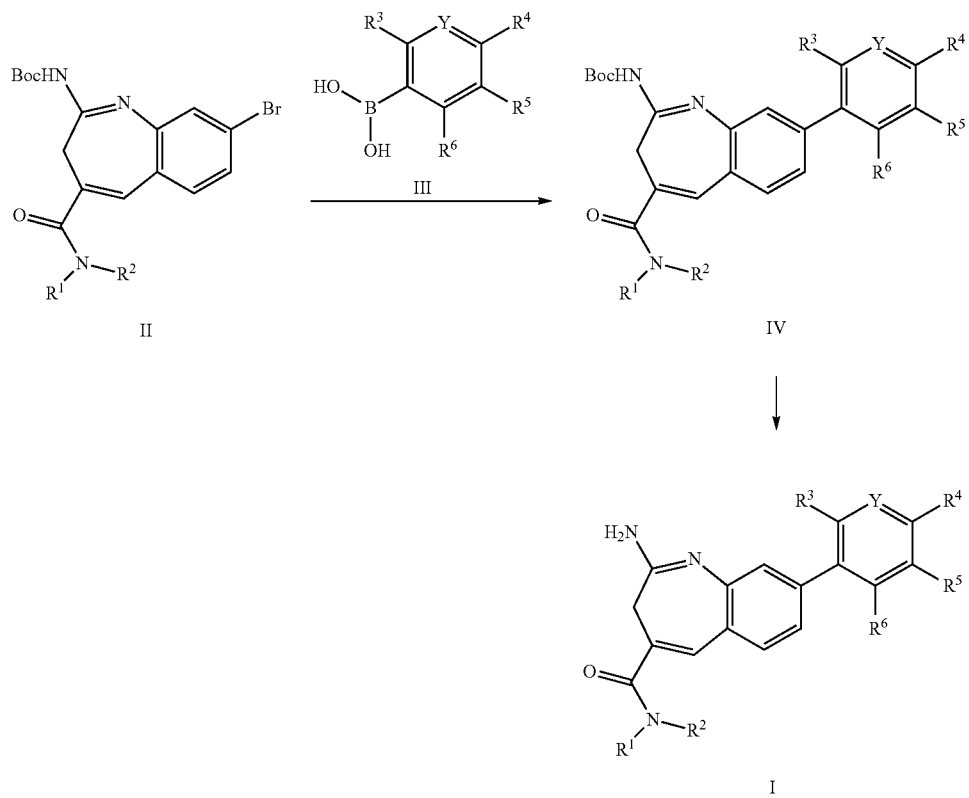

A compound of formula I can be prepared according to Scheme 1. A Suzuki coupling between bromide II and boronic acid III gives compound IV. Boc deprotection of compound IV gives a compound of formula I.

Pd-mediated Suzuki coupling between bromide II, prepared in analogy to compound G described in Scheme 3 and a selected aryl or heteroaryl boronic acid III using e.g. $Pd(dppf)_2Cl_2$ as catalyst in a solvent like 1,4-dioxane in presence of a base like sodium carbonate under nitrogen atmosphere and at ambient or elevated temperature gives compound IV.

A compound of formula I can be prepared by Boc deprotection of compound IV with TFA in dichloromethane and subsequent purification by prep-HPLC.

An alternative general synthetic route for the preparation of the compounds of formula I is depicted in Scheme 2.

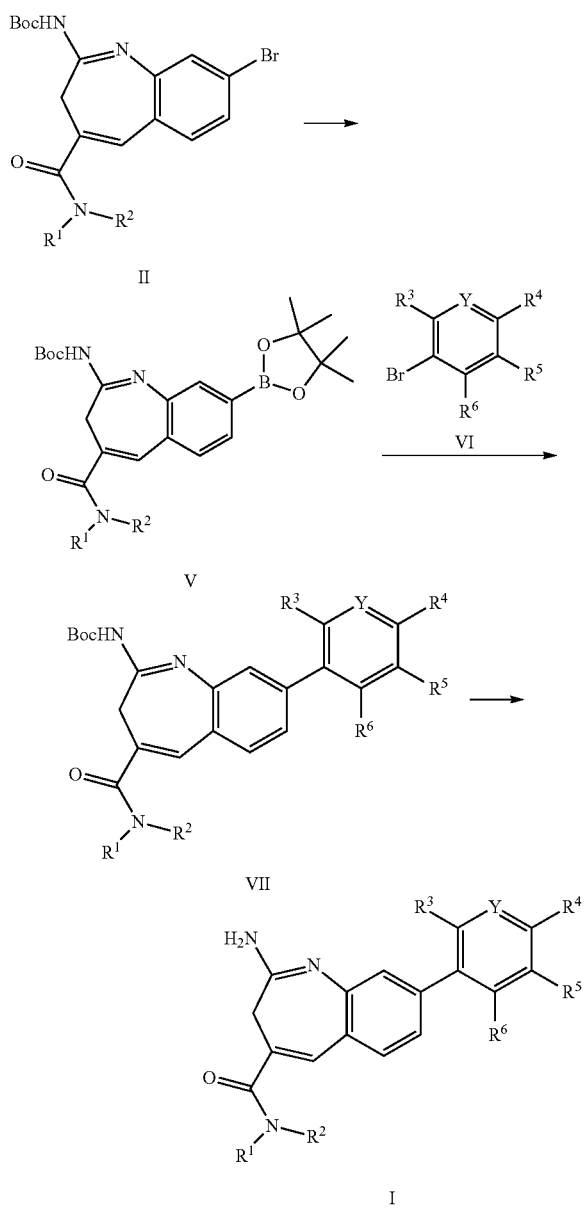

Scheme 2

A compound of formula I can also be prepared according to Scheme 2. Palladium catalyzed transformation of aryl bromide II gives aryl boronic acid ester V. A Suzuki coupling between boronic acid pinacol ester V and a selected aryl bromide or heteroaryl bromide VI gives compound VII. Boc deprotection of compound VII gives a compound of formula I.

Boronic acid pinacol ester V can be prepared by reacting bromide II with bis(pinacolato)diboron and Pd(dppf)$_2$Cl$_2$ under nitrogen atmosphere and at elevated temperatures. The reaction is typically running for several hours in a solvent like 1,4-dioxane to give compound V as a solution, which is used directly in the next step.

The above solution of boronic acid pinacol ester V is further reacted with another selected aryl bromide or heteroaryl bromide VI using typical Suzuki coupling conditions (catalytic Pd(dppf)$_2$Cl$_2$, sodium carbonate and elevated temperatures) under nitrogen atmosphere for several hours. Compound VII is obtained after chromatographic purification.

A compound of formula I can be prepared by Boc deprotection of compound VII with TFA in dichloromethane and subsequent purification by prep-HPLC.

If one of the starting materials contains one or more functional groups which are not stable or are reactive under the reaction conditions of one or more reaction steps, appropriate protecting groups (PG) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art.

If one or more compounds of the formula contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

As described herein before, the compounds of formula I of the present invention can be used as medicaments for the treatment of diseases which are mediated by TLR agonists, in particular for the treatment of diseases which are mediated by TLR8 agonists.

The compounds defined in the present invention are agonists of TLR8 receptors in cellular assays in vitro. Accordingly, the compounds of the present invention are expected to be potentially useful agents in the treatment of diseases or medical conditions that may benefit from the activation of the immune system via TLR8 agonists. They are useful in the treatment or prevention of diseases such as cancer, autoimmune diseases, inflammation, sepsis, allergy, asthma, graft rejection, graft-versus-host disease, immunodeficiencies, and infectious diseases.

In more detail, the compounds of formula I of the present invention are useful in oncology, i.e. they may be used in the treatment of common cancers including bladder cancer, head and neck cancer, prostate cancer, colorectal cancer, kidney cancer, breast cancer, lung cancer, ovarian cancer, cervical cancer, liver cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The compounds of formula I of the present invention are also useful in the treatment of autoimmune diseases. An "autoimmune disease" is a disease or disorder arising from and directed against an individual's own tissues or organs or a co-segregate or manifestation thereof or resulting condition therefrom. "Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). In a particular aspect, the autoimmune disease is associated with the skin, muscle tissue, and/or connective tissue.

Particular autoimmune diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases, ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)), allergic conditions and responses, food allergies, drug allergies, insect allergies, rare allergic disorders such as mastocytosis, allergic reaction, eczema including allergic or atopic eczema, asthma such as bronchial asthma and auto-immune asthma, conditions involving infiltration of myeloid cells and T cells and chronic inflammatory responses:

The compounds of formula I of the present invention are also useful in the treatment of infectious diseases. Thus, they may be useful in the treatment of viral diseases, in particular for diseases caused by infection with viruses selected from the group consisting of papilloma viruses, such as human papilloma virus (HPV) and those that cause genital warts, common warts and plantar warts, herpes simplex virus (HSV), molluscum contagiosum, hepatitis B virus (HBV), hepatitis C virus (HCV), Dengue virus, variola virus, human immunodeficiency virus (HIV), cytomegalovirus (CMV), varicella zoster virus (VZV), rhinovirus, enterovirus, adenovirus, coronavirus (e.g. SARS), influenza, mumps and parainfluenza.

They may also be useful in the treatment of bacterial diseases, in particular for diseases caused by infection with bacteria selected from the group consisting of *mycobacterium* such as *mycobacterium tuberculosis, mycobacterium avium* and *mycobacterium leprae*. The compounds of formula I of the present invention may further be useful in the treatment of other infectious diseases, such as chlamydia, fungal diseases, in particular fungal diseases selected from the group consisting of candidiasis, aspergillosis and cryptococcal meningitis, and parasitic diseases such as *Pneumocystis carnii*, pneumonia, cryptosporidiosis, histoplasmosis, toxoplasmosis, trypanosome infection and leishmaniasis.

Thus, the expression "diseases which are mediated by TLR agonists" means diseases which may be treated by activation of the immune system with TLR8 agonists, such as cancer, autoimmune diseases, inflammation, sepsis, allergy, asthma, graft rejection, graft-versus-host disease, immunodeficiencies, and infectious diseases. In particular, the expression "diseases which are mediated by TLR agonists" means cancer, autoimmune diseases, inflammation, sepsis, allergy, asthma, graft rejection, graft-versus-host disease, immunodeficiencies, and infectious diseases. Particularly, the expression "diseases which are mediated by TLR agonists" means cancer or infectious diseases.

In a particular aspect, the expression "which are mediated by TLR agonists" relates to cancer selected from the group consisting of bladder cancer, head and neck cancer, liver cancer, prostate cancer, colorectal cancer, kidney cancer, breast cancer, lung cancer, ovarian cancer, cervical cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The invention also relates to pharmaceutical compositions comprising a compound of formula I as defined above and a pharmaceutically acceptable carrier and/or adjuvant. More specifically, the invention relates to pharmaceutical compositions useful for the treatment of diseases which are which are mediated by TLR agonists.

Further, the invention relates to compounds of formula I as defined above for use as therapeutically active substances, particularly as therapeutically active substances for the treatment of diseases which are which are mediated by TLR agonists. In particular, the invention relates to compounds of formula I for use in the treatment of cancers or autoimmune diseases or infectious diseases selected from the group consisting of viral diseases, bacterial diseases, fungal diseases and parasitic diseases.

In another aspect, the invention relates to a method for the treatment a of diseases which are mediated by TLR agonists, which method comprises administering a therapeutically active amount of a compound of formula I to a human being or animal. In particular, the invention relates to a method for the treatment of cancers and infectious diseases selected from the group consisting of viral diseases, bacterial diseases, fungal diseases and parasitic diseases.

The invention further relates to the use of compounds of formula I as defined above for the treatment of diseases which are mediated by TLR agonists.

In addition, the invention relates to the use of compounds of formula I as defined above for the preparation of medicaments for the treatment of diseases which are mediated by TLR agonists. In particular, the invention relates to the use of compounds of formula I as defined above for the preparation of medicaments for the treatment of cancers or autoimmune diseases or infectious diseases selected from the group consisting of viral diseases, bacterial diseases, fungal diseases and parasitic diseases.

In a further aspect, compounds of formula I can be in combination with one or more additional treatment modalities in a regimen for the treatment of cancer.

Combination therapy encompasses, in addition to the administration of a compound of the invention, the adjunctive use of one or more modalities that are effective in the treatment of cancer. Such modalities include, but are not limited to, chemotherapeutic agents, immunotherapeutics, anti-angiogenic agents, cytokines, hormones, antibodies, polynucleotides, radiation and photodynamic therapeutic agents. In a specific aspect, combination therapy can be used to prevent the recurrence of cancer, inhibit metastasis, or inhibit the growth and/or spread of cancer or metastasis. As used herein, "in combination with" means that the compound of formula I is administered as part of a treatment regimen that comprises one or more additional treatment modalities as mentioned above. The invention thus also relates to a method for the treatment of cancer, which method comprises administering a therapeutically active amount of a compound of formula I in combination with one or more other pharmaceutically active compounds to a human being or animal.

Compounds of formula I can be used alone or in combination with one or more additional treatment modalities in treating autoimmune diseases.

Combination therapy encompasses, in addition to the administration of a compound of the invention, the adjunctive use of one or more modalities that aid in the prevention or treatment of autoimmune diseases. Such modalities include, but are not limited to, chemotherapeutic agents, immunotherapeutics, anti-angiogenic agents, cytokines, hormones, antibodies, polynucleotides, radiation and photodynamic therapeutic agents. As used herein, "in combination with" means that the compound of formula I is administered as part of a treatment regimen that comprises one or more additional treatment modalities as mentioned above. The invention thus also relates to a method for the treatment of autoimmune diseases, which method comprises administering a therapeutically active amount of a compound of formula I in combination with one or more other pharmaceutically active compounds to a human being or animal.

In a further aspect, compounds of formula I can be used alone or in combination with one or more additional treatment modalities in treating infectious diseases.

Combination therapy encompasses, in addition to the administration of a compound of the invention, the adjunctive use of one or more modalities that aid in the prevention or treatment of infectious diseases. Such modalities include, but are not limited to, antiviral agents, antibiotics, and anti-fungal agents. As used herein, "in combination with" means that the compound of formula I is administered as part of a treatment regimen that comprises one or more additional treatment modalities as mentioned above. The invention thus also relates to a method for the treatment of infectious diseases, which method comprises administering a therapeutically active amount of a compound of formula I in combination with one or more other pharmaceutically active compounds to a human being or animal.

Pharmacological Test

The following tests were carried out in order to determine the activity of the compounds of formula I:

For TLR8 and TLR7 activity testing, HEK-Blue human TLR8 or TLR7 cells (Invivogen, San Diego, Calif., USA) are used, respectively. These cells are designed for studying the stimulation of human TLR8 or TLR7 by monitoring the activation of NF-κB. A SEAP (secreted embryonic alkaline phosphatase) reporter gene is placed under the control of the IFN-b minimal promoter fused to five NF-κB and AP-1-binding sites. Therefore the reporter expression is regulated by the NF-κB promoter upon stimulation of human TLR8 or TLR7 for 20 hours. The cell culture supernatant SEAP reporter activity was determined using Quanti Blue kit (Invivogen, San Diego, Calif., USA) at a wavelength of 640 nm, a detection medium that turns purple/blue in the presence of alkaline phosphatase. $EC_{50}$ values were determined using Activity Base analysis (ID Business Solution, Limited).

The compounds according to formula I have an activity ($EC_{50}$ value) in the above assay for human TLR8 in the range of 0.01 nM to 0.1 μM, more particularly of 0.01 nM to 0.04 μM, whereas the activity ($EC_{50}$ value) in the above assay for human TLR7 is greater than 1 μM, in the range of 3 μM to >100 μM, meaning the compounds show high selectivity towards human TLR8.

For example, the following compounds showed the following $EC_{50}$ values in the assay described above:

| Example | human TLR8 $EC_{50}$ [μM] | human TLR7 $EC_{50}$ [μM] |
| --- | --- | --- |
| 1 | 0.006 | 3 |
| 2 | 0.006 | 7 |
| 3 | 0.006 | >100 |
| 4 | 0.023 | 5 |
| 5 | 0.003 | 103 |
| 6 | 0.01 | 104 |
| 7 | 0.005 | 18 |
| 8 | 0.005 | 24 |
| 9 | 0.005 | 17 |
| 10 | 0.004 | 20 |
| 11 | 0.008 | 12 |
| 12 | 0.008 | 12 |
| 13 | 0.004 | 17 |
| 14 | 0.009 | >100 |
| 15 | 0.004 | 17 |
| 16 | 0.002 | 26 |
| 17 | 0.005 | >100 |
| 18 | 0.006 | >100 |
| 19 | 0.009 | 14 |
| 20 | 0.017 | 5 |
| 21 | 0.018 | >100 |
| 22 | 0.031 | 17 |
| 23 | 0.006 | 13 |

Pharmaceutical Compositions

The compounds of formula I and their pharmaceutically acceptable salts can be used as medicaments, e.g., in the form of pharmaceutical preparations for enteral, parenteral or topical administration. The compounds of formula I and their pharmaceutically acceptable salts may be administered by systemic (e.g., parenteral) or local (e.g., topical or intralesional injection) administration. In some instances, the pharmaceutical formulation is topically, parenterally, orally, vaginally, intrauterine, intranasal, or by inhalation administered. As described herein, certain tissues may be preferred targets for the TLR agonist. Thus, administration of the TLR agonist to lymph nodes, spleen, bone marrow, blood, as well as tissue exposed to virus, are preferred sites of administration.

In one aspect, the pharmaceutical formulation comprising the compounds of formula I or its pharmaceutically acceptable salts is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used.

Formulations of the compounds of formula I suitable for parenteral administration are generally formulated in USP water or water for injection and may further comprise pH buffers, salts bulking agents, preservatives, and other pharmaceutically acceptable excipients.

Transdermal administration is accomplished by application of a cream, rinse, gel, etc. capable of allowing the TLR agonist to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter. Administration via the transdermal and transmucosal routes may be continuous or pulsatile.

Pulmonary administration is accomplished by inhalation, and includes delivery routes such as intranasal, transbronchial and transalveolar routes. Formulations of compounds of formula I suitable for administration by inhalation including, but not limited to, liquid suspensions for forming aerosols as well as powder forms for dry powder inhalation delivery systems are provided. Devices suitable for administration by inhalation include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

The compounds of formula I and pharmaceutically acceptable salts thereof may also be administered orally, e.g., in the form of tablets, coated tablets, dragées, hard and soft gelatine capsules.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example C2

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example C3

Injection solutions can have the following composition:

| | |
|---|---|
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The following examples serve to illustrate the present invention in more detail. They are, however, not intended to limit its scope in any manner.

EXAMPLES

Abbreviations Used Therein:

Boc$_2$O=di-tert-butyl dicarbonate, Boc=t-butyl carbamate, CD$_3$OD=deuterated methanol, d=day, DIPEA=N,N-diisopropylethylamine, DCM=dichloromethane, DMAP: 4-dimethylaminopyridine, DMF-DMA: N,N-dimethylformamide dimethyl acetal, EA=ethylacetate or EtOAc, EC$_{50}$=half maximal effective concentration, EDCI=1-(3-Dimethylaminopropyl)-3-ethylcarbodiimide hydrochloride, h or hr=hour, HOBT=N-hydroxybenzotriazole, HPLC=high performance liquid chromatography, HPLC-UV=high performance liquid chromatography with ultraviolet detector, Hz=hertz, mg=milligram, MHz=megahertz, min=minute(s), mL=milliliter, mm=millimeter, mM=mmol/L, mmol=millimole, MS=mass spectrometry, MW=molecular weight, NMR=nuclear magnetic resonance, PE=petroleum ether, prep-HPLC=preparative high performance liquid chromatography, rt=room temperature, sat.=saturated, TEA=triethylamine, TFA=trifluoroacetic acid, THF=tetrahydrofuran, μM=micromole, μm=micrometer, UV=ultraviolet detector, OD=optical density, Pd(dppf)$_2$Cl$_2$= [1,1'-Bis(diphenylphosphino)-ferrocene]dichloropalladium (II), TLR8=toll-like receptor 8, TLR7=toll-like receptor 7, NF-κB=nuclear factor kappa-light-chain-enhancer of activated B cells, SEAP=secreted embryonic alkaline phosphatase, IFN-β=interferon-beta.

Example A—Preparation of Key Intermediate G tert-Butyl N-[8-bromo-4-(dipropylcarbamoyl)-3H-1-benzazepin-2-yl]carbamate A detailed synthetic route is provided in Scheme 3.

Scheme 3

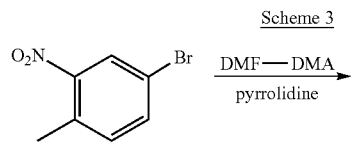

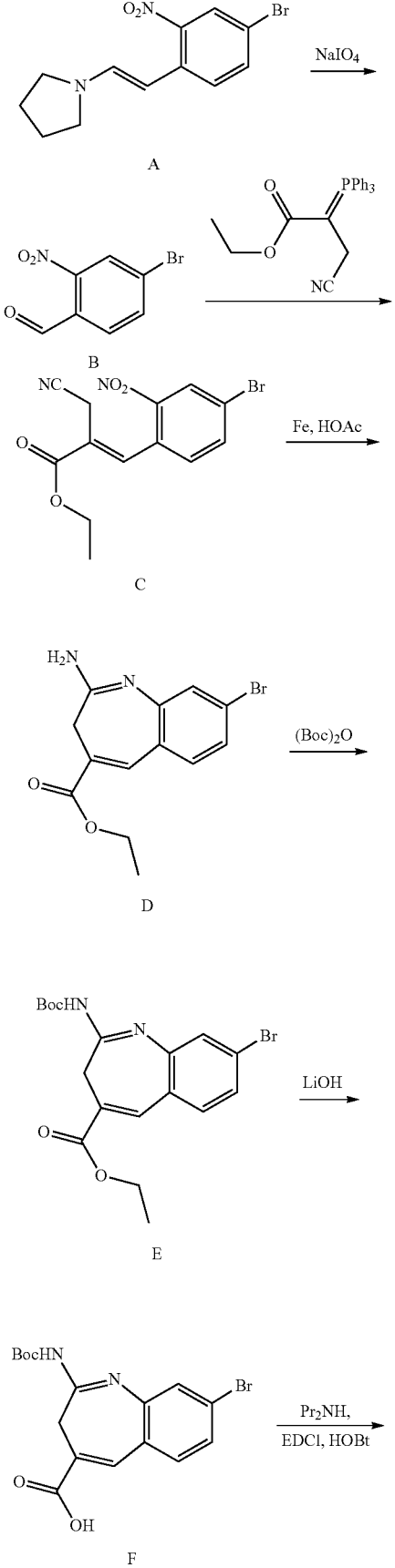

-continued

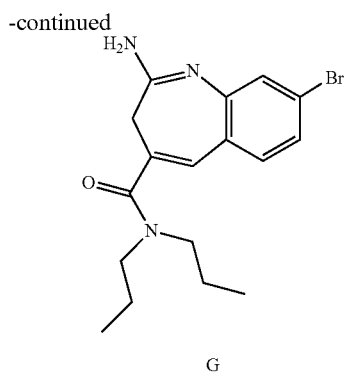

G a) Preparation of Compound A:

To a solution of 4-bromo-1-methyl-2-nitro-benzene (100 g, 0.46 mol) in DMF (1 L) was added successively pyrrolidine (39.6 g, 0.59 mol) and DMF-DMA (70 g, 0.59 mol). After the reaction mixture was stirred at 100° C. for 4 hours, the solvent was concentrated under reduced pressure to give 1-[(E)-2-(4-bromo-2-nitro-phenyl)vinyl]pyrrolidine (compound A, 137 g, crude) as brown oil which was used directly in the next step. MS: m/z=297 (M+H)$^+$.

b) Preparation of Compound B:

To a solution of 1-[(E)-2-(4-bromo-2-nitro-phenyl)vinyl]pyrrolidine (compound A, 137 g, 0.47 mol) in a mixture of THF (1.7 L) and water (2.0 L) was added NaIO$_4$ (298 g, 1.40 mol) in portions at 10° C. After the reaction mixture was stirred at 25° C. for 20 hours, it was filtered and the filtrate was extracted with EA (3 L). The separated organic layer was washed with brine, dried over anhydrous Na$_2$SO$_4$, filtered and concentrated to give the crude product. The crude product was purified by silica gel column chromatography using 5% ethyl acetate in PE to give 4-bromo-2-nitro-benzaldehyde (compound B, 66 g, 61%) as a yellow solid. MS: m/z=230 (M+H)$^+$.

c) Preparation of Compound C:

To a solution of 4-bromo-2-nitro-benzaldehyde (compound B, 65 g, 0.28 mol) in toluene (700 mL) was added ethyl 3-cyano-2-(triphenyl phosphoranylidene) propionate (120 g, 0.31 mol) at 25° C. After the reaction was stirred at 25° C. for 18 hours, the reaction mixture was concentrated. Then methanol (500 mL) was added. After the solution was kept in refrigerator for 4 hours, it was filtered to give 2-[1-(4-bromo-2-nitro-phenyl)-(E)-methylidene]-3-cyano-propionic acid ethyl ester (compound C, 75 g, 78%) as a white solid. MS: m/z=298 (M+H)$^+$.

d) Preparation of Compound D:

To a stirred solution of 2-[1-(4-bromo-2-nitro-phenyl)-meth-(E)-ylidene]-3-cyano-propionic acid ethyl ester (compound C, 75 g, 0.22 mol) in AcOH (1.1 L) was added Fe (74 g, 1.33 mol) at 80° C. After the reaction mixture was heated at 80° C. for 3 hours, the reaction mixture was filtered off through a celite pad. The celite pad was washed with acetic acid. The combined filtrates were concentrated in vacuo and basified with saturated NaHCO$_3$ solution (300 mL). Ethyl acetate (1 L) was then added and the mixture stirred. The undissolved material was further filtered off through a celite pad. The celite pad was washed with ethyl acetate (800 mL). After phase separation, the organic layer was collected and washed with water, dried over Na$_2$SO$_4$ and concentrated in vacuo to give the crude product. The crude product was further rinsed with diethyl ether (100 mL) to give ethyl 2-amino-8-bromo-3H-1-benzazepine-4-carboxylate (compound D, 50 g, 73%) as a light yellow solid. MS: m/z=309 (M+H)$^+$.

e) Preparation of Compound E:

To a solution of ethyl 2-amino-8-bromo-3H-1-benzazepine-4-carboxylate (compound D, 50 g, 0.16 mol) and TEA (26.1 g, 0.26 mol) in DCM (500 mL) was added a solution of Boc$_2$O (56.6 g, 0.26 mol) in DCM (100 mL) at 0-5° C. After the reaction was stirred at 25° C. for 42 hours, water (200 mL) was added. The organic layer was separated and washed with brine, dried over Na$_2$SO$_4$, filtered and concentrated. The residue was slurried in EA and PE and filtered to give ethyl 8-bromo-2-(tert-butoxycarbonylamino)-3H-1-benzazepine-4-carboxylate (compound E, 57 g, 86%) as a yellow solid. MS: m/z=409 (M+H)$^+$.

f) Preparation of Compound F:

To a solution of ethyl 8-bromo-2-(tert-butoxycarbonylamino)-3H-1-benzazepine-4-carboxylate (compound E, 10 g, 24.5 mmol) in THF (60 mL) was added aqueous LiOH (37 mL, 1M) in a solvent mixture of EtOH (18 mL) and water (18 mL). The reaction was stirred at 25° C. for 18 hours. A solution of LiOH (10 mL, 1M) in EtOH (5 mL) and water (5 mL) was added, and the reaction mixture was further stirred at 25° C. for 5 hours. After the reaction was acidified to pH=5 with 10% citric acid, the aqueous layer was extracted with EA. The organic layers were combined, dried over anhydrous Na$_2$SO$_4$, filtered, and concentrated to give 8-bromo-2-(tert-butoxycarbonylamino)-3H-1-benzazepine-4-carboxylic acid (compound F, 9.6 g, crude) as a yellow solid. MS: m/z=380 (M+H)$^+$.

g) Preparation of Compound G:

To a solution of 8-bromo-2-(tert-butoxycarbonylamino)-3H-1-benzazepine-4-carboxylic acid (compound F, 9.6 g, 25.3 mmol) in DCM (360 mL) was successively added EDCI (12 g, 63.1 mmol), HOBT (4.1 g, 30.3 mmol), DIPEA (13 g, 101 mmol) and DMAP (770 mg, 6.3 mmol) at 10° C. After the reaction mixture was stirred for 30 min at 25° C., N-propylpropan-1-amine (3.8 g, 37.9 mmol) was added. The reaction mixture was stirred at 25° C. for 3 hrs. Water was then added and the mixture was extracted with DCM. The solvent was concentrated under reduced pressure and the residue was purified by silica gel chromatography (PE:EA=5:1) to give tert-butyl N-[8-bromo-4-(dipropylcarbamoyl)-3H-1-benzazepin-2-yl]carbamate (compound G, 8.6 g, 73%) as a yellow solid. 1H-NMR (300 MHz, DMSO-d6): δ ppm=10.25-10.07 (m, 1H), 7.44-7.24 (m, 3H), 6.86-6.79 (m, 1H), 3.28-3.14 (m, 4H), 3.13-3.01 (m, 2H), 1.62-1.45 (m, 4H), 1.43 (s, 9H), 1.00-0.62 (m, 6H). MS: m/z=464 (M+H)+.

Example 1

2-Amino-N,N-dipropyl-8-(3-sulfamoylphenyl)-3H-1-benzazepine-4-carboxamide

Step 1: tert-butyl N-[4-(dipropylcarbamoyl)-8-(3-sulfamoylphenyl)-3H-1-benzazepin-2-yl]carbamate

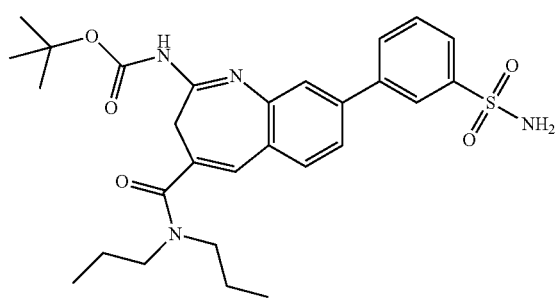 [SMILES: CCCN(CCC)C(=O)C1=Cc2ccc(-c3cccc(S(N)(=O)=O)c3)cc2N=C(NC(=O)OC(C)(C)C)C1]

In a microwave tube, tert-butyl N-[8-bromo-4-(dipropylcarbamoyl)-3H-1-benzazepin-2-yl]carbamate (compound G, 0.1 g, 215 µmol), 3-sulfamoylphenylboronic acid (86.6 mg, 431 µmol) and tetrakis(triphenylphosphine)palladium (0) (4.98 mg, 4.31 µmol) were dissolved under argon atmosphere in 1,2-dimethoxyethane (1.4 mL). Na$_2$CO$_3$ (2N aqueous solution, 323 µL, 646 µmol) was added and the reaction mixture was heated to 80° C. and stirred for 4 hrs. Water was added and the crude product suspension was extracted with ethyl acetate. The organic layer was dried over Na$_2$SO$_4$ and filtered. The solvent was evaporated in vacuo. The product was obtained as light yellow waxy solid (70 mg, 60%) after purification by flash chromatography (using silica gel column and an ethyl acetate/heptane gradient). $^1$H NMR (DMSO-d$_6$, 300 MHz): δ ppm=10.08 (br s, 1H), 8.19 (s, 1H), 7.97 (d, J=8.1 Hz, 1H), 7.80 (d, J=8.1 Hz, 1H), 7.44-7.74 (m, 4H), 7.42 (s, 2H), 6.91 (s, 1H), 3.20-3.34 (m, 4H), 3.12 (s, 2H), 1.45-1.63 (m, 4H), 1.44 (s, 9H), 0.70-0.94 (m, 6H). MS: m/z=541.3 (M+H)$^+$.

Step 2: 2-amino-N,N-dipropyl-8-(3-sulfamoylphenyl)-3H-1-benzazepine-4-carboxamide

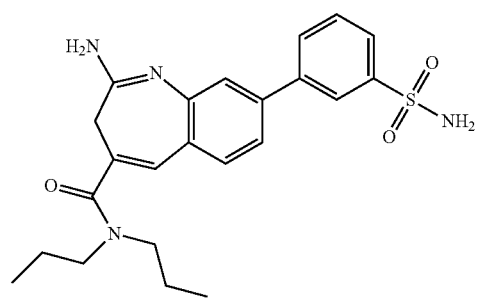 [SMILES: CCCN(CCC)C(=O)C1=Cc2ccc(-c3cccc(S(N)(=O)=O)c3)cc2N=C(N)C1]

To a solution of tert-butyl N-[4-(dipropylcarbamoyl)-8-(3-sulfamoylphenyl)-3H-1-benzazepin-2-yl]carbamate (69 mg, 126 µmol) in dichloromethane (2.3 ml) was added TFA (860 mg, 581 µl, 7.55 mmol). The light yellow solution was stirred at rt for 1 h. All volatiles were evaporated and the product was obtained after prep-HPLC as off-white solid (34 mg, 61%). $^1$H NMR (DMSO-d$_6$, 300 MHz): δ ppm=8.15 (dd, J=1.7, 1.7 Hz, 1H), 7.91 (m, 1H), 7.78 (m, 1H), 7.64 (dd, J=8.1 Hz, 1H), 7.35-7.45 (m, 4H), 7.27 (dd, J=8.1, 2.0 Hz, 1H), 6.82 (br s, 2H), 6.76 (s, 1H), 3.25-3.35 (m, 4H), 2.74 (s, 2H), 1.50-1.65 (m, 4H), 0.75-0.90 (m, 6H). MS: m/z=441.2 (M+H)$^+$.

Example 2

2-Amino-8-[3-(2-hydroxyethylsulfamoyl)phenyl]-N,N-dipropyl-3H-1-benzazepine-4-carboxamide The title compound was prepared according to the general synthetic routes shown in Scheme 1. A detailed synthetic route is provided in Scheme 4.

Scheme 4:

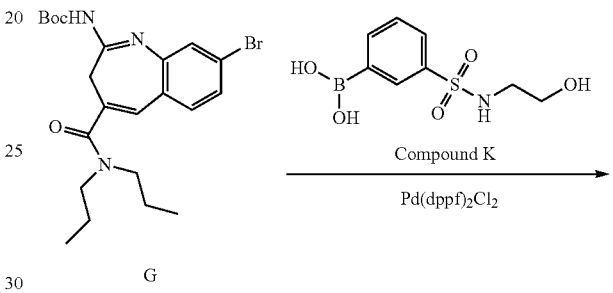

Example 2

Step 1: Preparation of Compound L

To a mixture of tert-butyl N-[8-bromo-4-(dipropylcarbamoyl)-3H-1-benzazepin-2-yl]carbamate (compound G, 110 mg, 0.215 mmol) and [3-(2-hydroxyethylsulfamoyl)phenyl]-boronic acid (compound K, 70 mg, 0.28 mmol) in a mixture of DMF (4.5 mL) and water (0.9 ml) were added Pd(dppf)$_2$Cl$_2$ (12 mg) and Na$_2$CO$_3$ (113 mg, 1.07 mmol). The reaction was degassed and then charged with nitrogen for three times. The reaction mixture was stirred under nitrogen at 85-90° C. for 2 hrs. After the undissolved material was filtered, water (3 mL) and EtOAc (3 mL) were added. The organic layer was separated and concentrated to give crude tert-butyl N-[4-(dipropylcarbamoyl)-8-[3-(2-hydroxyethylsulfamoyl)phenyl]-3H-1-benzazepin-2-yl]carbamate (compound L, 80 mg). MS: m/z=585 (M+H)$^+$.

Step 2: Preparation of Example 2

To a solution of tert-butyl N-[4-(dipropylcarbamoyl)-8-[3-(2-hydroxyethyl sulfamoyl)-phenyl]-3H-1-benzazepin-2-yl]carbamate (compound L, 80 mg) in DCM (2 mL) was added TFA (0.5 mL) in DCM (0.5 mL) at 0° C. The mixture was stirred at 25° C. for 1.5 hours. Solvent was removed and the residue was purified by prep-HPLC to give 2-amino-8-[3-(2-hydroxyethyl-sulfamoyl)]-N,N-dipropyl-3H-1-benzazepine-4-carboxamide (Example 2) as a light yellow solid (19 mg, 15%). $^1$H NMR (CD$_3$OD, 400 MHz): δ ppm=8.53 (s, 1H), 8.18 (t, J=1.6 Hz, 1H), 7.88-8.02 (m, 2H), 7.66-7.80 (m, 1H), 7.53-7.64 (m, 2H), 6.92-7.06 (m, 1H), 3.58 (t, J=6.0 Hz, 2H), 3.47 (br. s, 6H), 3.03 (t, J=5.9 Hz, 2H), 1.72 (dq, J=14.9, 7.3 Hz, 4H), 0.97 (br. s., 6H). MS: m/z=485 (M+H)$^+$.

Example 3

2-amino-N,N-dipropyl-8-(3-pyrrolidin-1-ylsulfonyl-phenyl)-3H-1-benzazepine-4-carboxamide

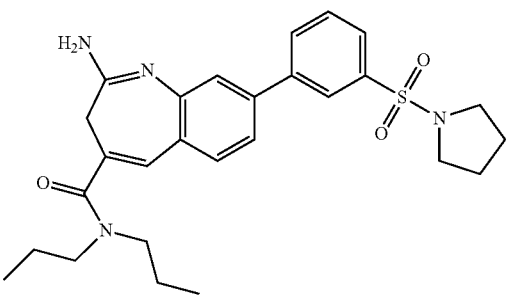 [SMILES: CCCN(CCC)C(=O)C1=Cc2ccc(-c3cccc(S(=O)(=O)N4CCCC4)c3)cc2N=C(N)C1]

The title compound was prepared in two steps in analogy to Example 2 by using (3-pyrrolidin-1-ylsulfonylphenyl) boronic acid instead of [3-(2-hydroxyethylsulfamoyl)phenyl]-boronic acid (compound K). Example 3 was obtained as a light yellow solid (36 mg). $^1$H NMR (CD$_3$OD, 400 MHz): δ ppm=8.53 (s, 1H), 8.18 (t, J=1.6 Hz, 1H), 7.87-8.02 (m, 2H), 7.67-7.79 (m, 1H), 7.50-7.63 (m, 2H), 6.94-7.08 (m, 1H), 3.58 (t, J=6.0 Hz, 2H), 3.05-3.47 (br., 8H), 3.03 (t, J=5.9 Hz, 2H), 1.61-1.84 (m, 6H), 0.97 (br. s., 6H). MS: m/z=495 (M+H)$^+$.

Example 4

2-Amino-N,N-dipropyl-8-(5-sulfamoyl-3-pyridyl)-3H-1-benzazepine-4-carboxamide

The title compound was prepared according to the general synthetic route shown in Scheme 2. A detailed synthetic route is provided in Scheme 5.

Scheme 5:

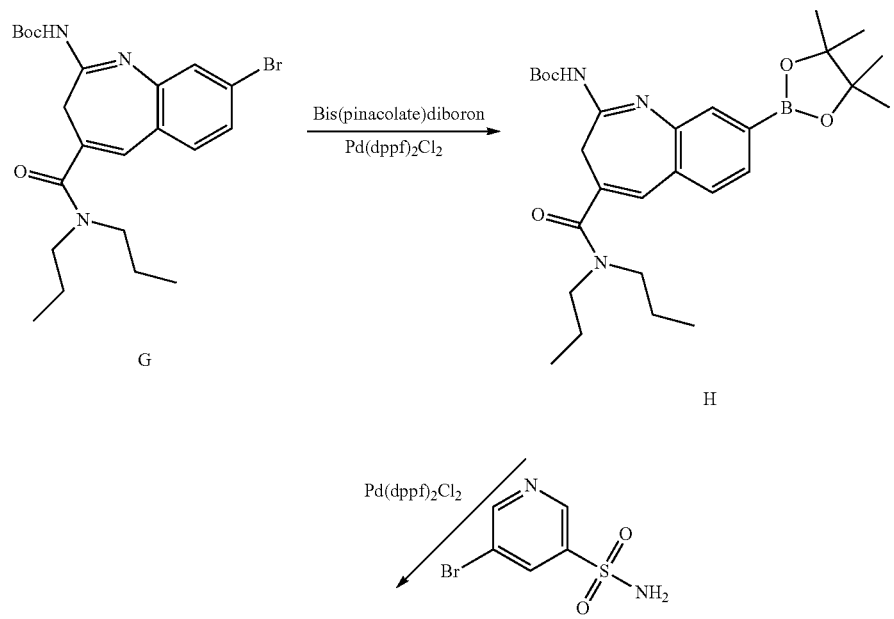

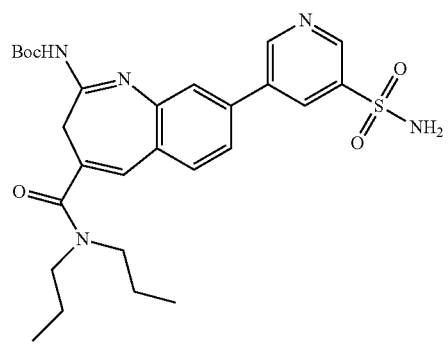

J

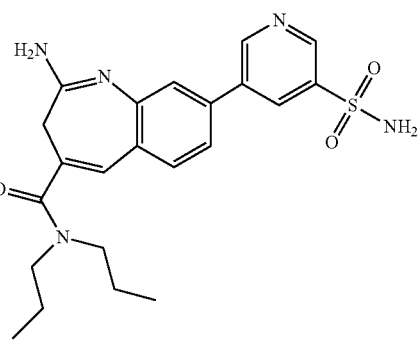

Example 5

Step 1: Preparation of Compound H

To a stirred solution of tert-butyl N-[8-bromo-4-(dipropylcarbamoyl)-3H-1-benzazepin-2-yl]carbamate (compound G, 200 mg, 0.42 mmol) in 1,4-dioxane (3 mL) was added bis(pinacolato)diboron (112 mg, 0.44 mmol), potassium acetate (82 mg, 0.84 mmol) and Pd(dppf)$_2$Cl$_2$ (61 mg, 0.084 mmol) under N$_2$ atmosphere. Then the reaction mixture was stirred at 80° C. for 3 hours to give a solution of tert-butyl N-[4-(dipropylcarbamoyl)-8-(4,4,5,5-tetramethyl-1,3,2-dioxaborolan-2-yl)-3H-1-benzazepin-2-yl]carbamate (compound H) which can be used in the next step without further purification. MS: m/z=512 (M+H)$^+$.

Step 2: Preparation of Compound J

To the above 1,4-dioxane solution of tert-butyl N-[4-(dipropylcarbamoyl)-8-(4,4,5,5-tetramethyl-1,3,2-dioxaborolan-2-yl)-3H-1-benzazepin-2-yl]carbamate (compound H) was added 5-bromopyridine-3-sulfonamide (CAS Registry No. 62009-33-0, 120 mg, 0.51 mmol), sodium carbonate (89 mg, 0.84 mmol), water (1 mL) and Pd(dppf)$_2$Cl$_2$ (61 mg, 0.084 mmol) under N$_2$ atmosphere. After the reaction mixture was stirred at 100° C. for 2 hours, the undissolved material was filtered. The filtrate was diluted with water (3 mL) and EtOAc (3 mL), and the organic layer was separated, dried over Na$_2$SO$_4$, and concentrated to give the crude product. The crude product was purified by prep-HPLC to give tert-butyl N-[4-(dipropylcarbamoyl)-8-(5-sulfamoyl-3-pyridyl)-3H-1-benzazepin-2-yl]carbamate (compound J, 80 mg). MS: m/z=542 (M+H)$^+$.

Step 3: Preparation of Example 4

To a solution of tert-butyl N-[4-(dipropylcarbamoyl)-8-(5-sulfamoyl-3-pyridyl)-3H-1-benzazepin-2-yl]carbamate (compound J, 80 mg, 0.15 mmol) in DCM (2 mL) was added TFA (0.5 mL) in DCM (0.5 mL) at 0° C. After the reaction mixture was stirred at 25° C. for 1.5 hours, solvent was removed and the residue was purified by prep-HPLC to give 2-amino-N,N-dipropyl-8-(5-sulfamoyl-3-pyridyl)-3H-1-benzazepine-4-carboxamide (Example 4) as a withe solid (8.2 mg, 13%). $^1$H NMR (CD$_3$CN, 400 MHz) δ ppm=12.86 (br. s., 1H), 9.49-9.21 (m, 1H), 9.18 (br. s., 1H), 9.08 (s, 1H), 8.80 (br. s., 1H), 7.88 (s, 1H), 7.74 (br. s., 1H), 7.60 (d, J=8.3 Hz, 1H), 7.02 (br. s., 2H), 6.91 (s, 1H), 3.43 (br. s., 4H), 3.32 (br. s., 2H), 1.66 (d, J=6.8 Hz, 4H), 0.90 (br. s., 6H). MS: m/z=442 (M+H)$^+$.

Example 5

2-Amino-8-[3-(3-hydroxypyrrolidin-1-yl)sulfonylphenyl]-N,N-dipropyl-3H-1-benzazepine-4-carboxamide

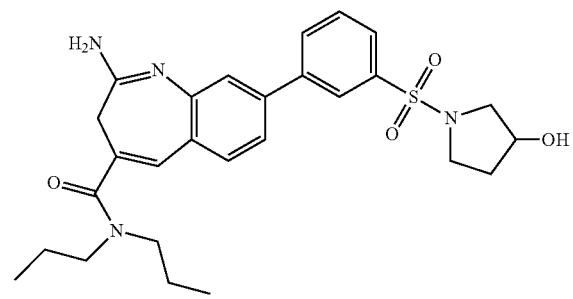 [SMILES: CCCN(CCC)C(=O)C1=Cc2ccc(-c3cccc(S(=O)(=O)N4CCC(O)C4)c3)cc2N=C(N)C1]

The title compound was prepared in 2 steps in analogy to Example 4 by using 1-(3-bromophenyl)sulfonylpyrrolidin-3-ol (Compound 5A) instead of 5-bromopyridine-3-sulfonamide. Example 5 was obtained as a light yellow solid (45 mg). $^1$H NMR (CD$_3$OD, 400 MHz): δ ppm=8.53 (br. s., 1H), 8.11 (s, 1H), 8.00 (d, J=7.5 Hz, 1H), 7.88 (d, J=8.0 Hz, 1H), 7.68-7.81 (m, 1H), 7.50-7.61 (m, 2H), 6.93-7.06 (m, 1H), 4.32 (dd, J=4.5, 2.5 Hz, 1H), 3.36-3.53 (m, 6H), 3.26 (d, J=10.8 Hz, 2H), 1.61-2.02 (m, 8H), 0.95 ppm (br. s., 6H). MS: m/z=511 (M+H)$^+$.

Preparation of 1-(3-bromophenyl)sulfonylpyrrolidin-3-ol (Compound 5A)

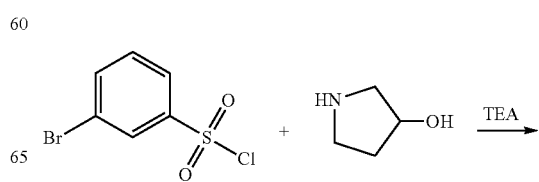

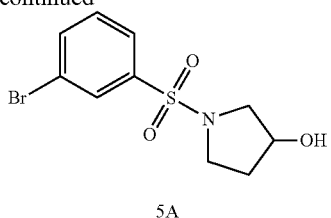

5A

To a stirred solution of DCM (10 ml) and TEA (505 mg, 5 mmol) was added pyrrolidin-3-ol (170 mg, 2 mmol) at 25° C., followed by 3-bromobenzenesulfonyl chloride (370 mg, 1.5 mmol) in DCM (2 mL). Then the mixture was stirred for additional 2 hrs at room temperature. The reaction mixture was washed with brine (10 mL) and the organic layer was dried over $Na_2SO_4$, and concentrated in vacuo to give crude 1-(3-bromophenyl)sulfonylpyrrolidin-3-ol (Compound 5-A, 420 mg) which can be used in the next step without further purification. MS: m/z=306 $(M+H)^+$.

Example 6

2-Amino-8-[4-(3-hydroxypyrrolidin-1-yl)sulfonyl-phenyl]-N,N-dipropyl-3H-1-benzazepine-4-carbox-amide

6A

Compound 6A was prepared in analogy to compound 5A of Example 5 by using 4-bromobenzenesulfonyl chloride instead of 3-bromobenzenesulfonyl chloride. MS: m/z=306 $(M+H)^+$.

Example 7

2-Amino-8-[3-[(3R)-3-hydroxypyrrolidin-1-yl]sulfo-nylphenyl]-N,N-dipropyl-3H-1-benzazepine-4-car-boxamide

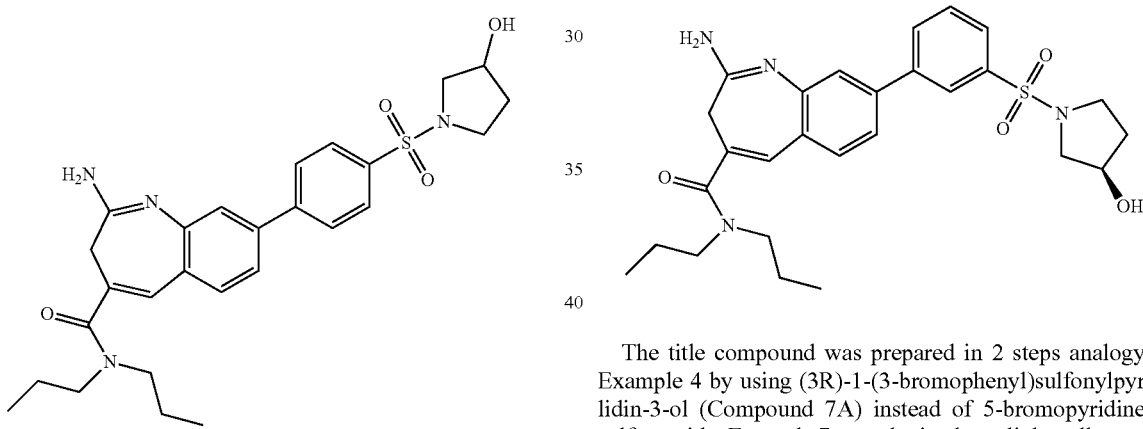

The title compound was prepared in 2 steps in analogy to Example 4 by using 1-(4-bromophenyl)sulfonylpyrrolidin-3-ol (Compound 6A) instead of 5-bromopyridine-3-sulfo-namide. Example 6 was obtained as a light yellow solid (55 mg). $^1H$ NMR ($CD_3OD$, 400 MHz): δ ppm=8.55 (s, 1H), 7.84-8.01 (m, 4H), 7.43-7.58 (m, 2H), 6.95 (s, 1H), 4.33 (d, J=2.5 Hz, 1H), 3.35-3.55 (m, 6H), 3.24 (d, J=10.8 Hz, 2H), 1.58-2.00 (m, 8H), 0.95 (br. s., 6H). MS: m/z=511 $(M+H)^+$.

Preparation of 1-(4-bromophenyl)sulfonylpyrrolidin-3-ol (Compound 6A)

The title compound was prepared in 2 steps analogy to Example 4 by using (3R)-1-(3-bromophenyl)sulfonylpyrro-lidin-3-ol (Compound 7A) instead of 5-bromopyridine-3-sulfonamide. Example 7 was obtained as a light yellow solid (20 mg). $^1H$ NMR ($CD_3OD$, 400 MHz): δ ppm=8.09 (t, J=1.6 Hz, 1H), 7.98 (d, J=7.8 Hz, 1H), 7.80-7.90 (m, 1H), 7.65-7.77 (m, 1H), 7.45-7.51 (m, 2H), 7.35-7.43 (m, 1H), 6.91 (s, 1H), 4.32 (dt, J=4.8, 2.4 Hz, 1H), 3.36-3.53 (m, 6H), 3.26 (d, J=11.3 Hz, 1H), 2.83-2.97 (m, 1H), 1.61-2.03 (m, 8H), 0.93 (br. s., 6H). MS: m/z=511 $(M+H)^+$.

Preparation of (3R)-1-(3-bromophenyl)sulfonylpyr-rolidin-3-ol (Compound 7A)

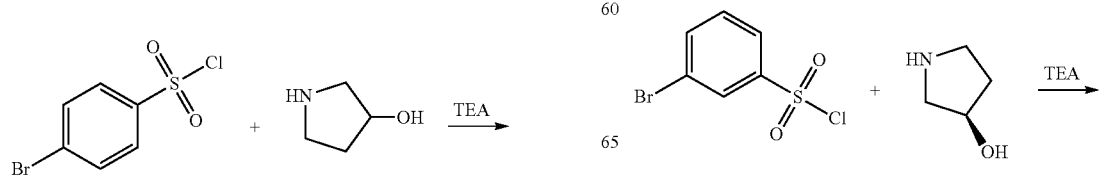

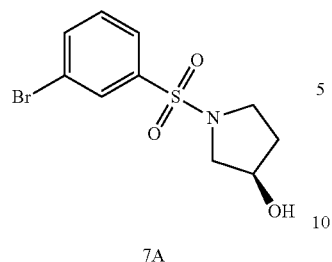

7A

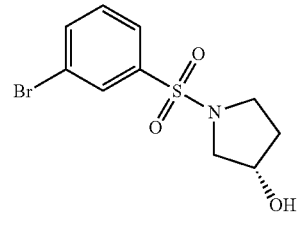

8A

Compound 7A was prepared in analogy to compound 5A of Example 5 by using (3R)-pyrrolidin-3-ol instead of pyrrolidin-3-ol. MS: m/z=306 (M+H)+.

Compound 8A was prepared in analogy to compound 5A of Example 5 by using (3S)-pyrrolidin-3-ol instead of pyrrolidin-3-ol. MS: m/z=306 (M+H)+.

Example 8

2-Amino-8-[3-[(3S)-3-hydroxypyrrolidin-1-yl]sulfonylphenyl]-N,N-dipropyl-3H-1-benzazepine-4-carboxamide Example 9

2-Amino-8-[3-(3-hydroxyazetidin-1-yl)sulfonylphenyl]-N,N-dipropyl-3H-1-benzazepine-4-carboxamide

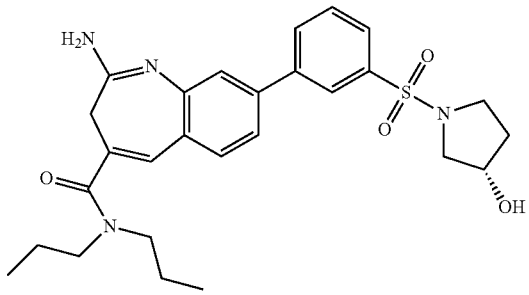 [SMILES: CCCN(CCC)C(=O)C1=Cc2ccc(-c3cccc(S(=O)(=O)N4CC[C@H](O)C4)c3)cc2N=C(N)C1]

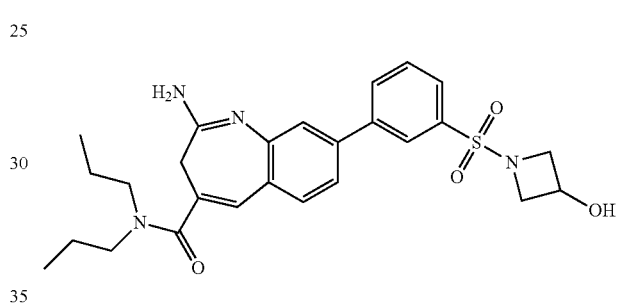

The title compound was prepared in 2 steps in analogy to Example 4 by using (3S)-1-(3-bromophenyl)sulfonylpyrrolidin-3-ol (Compound 8A) instead of 5-bromopyridine-3-sulfonamide. Example 8 was obtained as a light yellow solid (35 mg). $^1$H NMR (CD$_3$OD, 400 MHz): δ ppm=8.09 (t, J=1.6 Hz, 1H), 7.98 (d, J=7.8 Hz, 1H), 7.81-7.90 (m, 1H), 7.65-7.78 (m, 1H), 7.35-7.54 (m, 3H), 6.91 (s, 1H), 4.32 (t, J=4.6, 2.6 Hz, 1H), 3.37-3.54 (m, 6H), 3.23-3.29 (m, 1H), 2.86-2.94 (m, 1H), 1.57-2.02 (m, 8H), 0.93 (br. s., 6H). MS: m/z=511 (M+H)+.

The title compound was prepared in 2 steps in analogy to Example 4 by using 1-(3-bromophenyl)sulfonylazetidin-3-ol (Compound 9A) instead of 5-bromopyridine-3-sulfonamide. Example 9 was obtained as a light yellow solid (10 mg). $^1$H NMR (CD$_3$OD, 400 MHz): δ ppm=8.00-8.12 (m, 2H), 7.74-7.91 (m, 2H), 7.35-7.55 (m, 3H), 6.91 (s, 1H), 4.34-4.50 (m, 1H), 4.02 (dd, J=8.9, 6.7 Hz, 2H), 3.39-3.61 (m, 6H), 2.82-2.99 (m, 2H), 1.59-1.81 (m, 4H), 0.92 (br. s., 6H). MS: m/z=497 (M+H)+.

Preparation of 1-(3-bromophenyl)sulfonylazetidin-3-ol (Compound 9A)

Preparation of (3S)-1-(3-bromophenyl)sulfonylpyrrolidin-3-ol (Compound 8A)

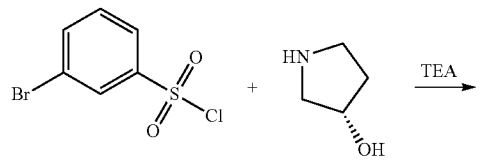

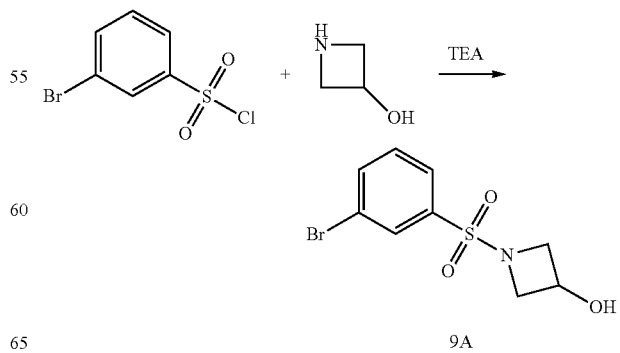

9A

Compound 9A was prepared in analogy to compound 5A of Example 5 by using azetidin-3-ol instead of pyrrolidin-3-ol. MS: m/z=292 (M+H)⁺.

Example 10

2-Amino-8-[3-[2-hydroxyethyl(methyl)sulfamoyl]phenyl]-N,N-dipropyl-3H-1-benzazepine-4-carboxamide

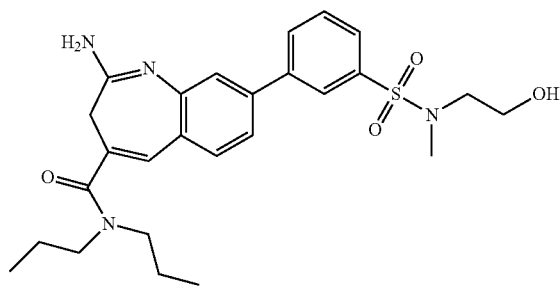 [SMILES: CCCN(CCC)C(=O)C1=Cc2ccc(-c3cccc(S(=O)(=O)N(C)CCO)c3)cc2N=C(N)C1]

The title compound was prepared in two steps in analogy to Example 4 by using 3-bromo-N-(2-hydroxyethyl)-N-methyl-benzenesulfonamide (Compound 10A) instead of 5-bromopyridine-3-sulfonamide. Example 10 was obtained as a light yellow solid (35 mg). ¹H NMR (CD₃OD, 400 MHz): δ ppm=8.06 (t, J=1.6 Hz, 1H), 7.96-8.01 (m, 1H), 7.83 (dt, J=8.2, 1.2 Hz, 1H), 7.66-7.77 (m, 1H), 7.30-7.52 (m, 3H), 6.91 (s, 1H), 3.72 (t, J 5.8 Hz, 2H), 3.38-3.55 (m, 4H), 3.09-3.24 (m, 4H), 2.88 (s, 3H), 1.55-1.84 (m, 4H), 0.93 (br. s., 6H). MS: m/z=499 (M+H)⁺.

Preparation of 3-bromo-N-(2-hydroxyethyl)-N-methyl-benzenesulfonamide (Compound 10A)

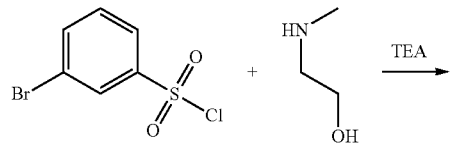

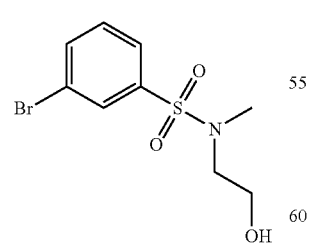

10A

Compound 10A was prepared in analogy to compound 5A of Example 5 by using 2-(methylamino)ethanol instead of pyrrolidin-3-ol. MS: m/z=294 (M+H)⁺.

Example 11

2-Amino-8-[3-[2-(2-hydroxyethoxy)ethylsulfamoyl]phenyl]-N,N-dipropyl-3H-1-benzazepine-4-carboxamide

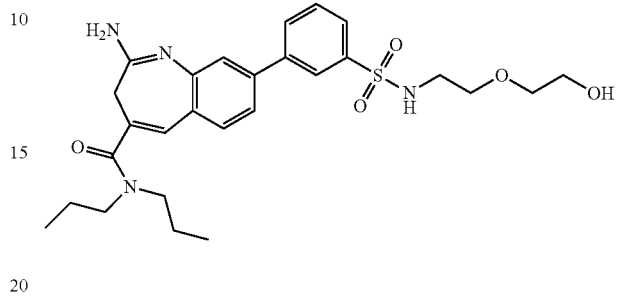

The title compound was prepared in two steps in analogy to Example 4 by using 3-bromo-N-[2-(2-hydroxyethoxy)ethyl]benzenesulfonamide (Compound 11A) instead of 5-bromopyridine-3-sulfonamide. Example 11 was obtained as a light yellow solid (20 mg). ¹H NMR (CD₃OD, 400 MHz): δ ppm=8.18 (t, J=1.8 Hz, 1H), 7.95 (d, J=7.8 Hz, 1H), 7.87 (d, J=8.3 Hz, 1H), 7.62-7.73 (m, 1H), 7.33-7.54 (m, 3H), 6.91 (s, 1H), 3.58-3.67 (m, 2H), 3.25-3.54 (m, 8H), 3.14 (t, J=5.3 Hz, 2H), 2.81-2.96 (m, 2H), 1.60-1.78 (m, 4H), 0.94 (br. s., 6H). MS: m/z=529 (M+H)⁺.

Preparation of 3-bromo-N-[2-(2-hydroxyethoxy)ethyl]benzenesulfonamide (Compound 11A)

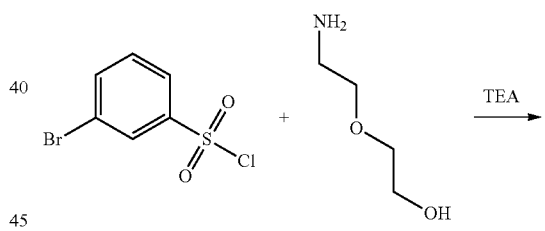

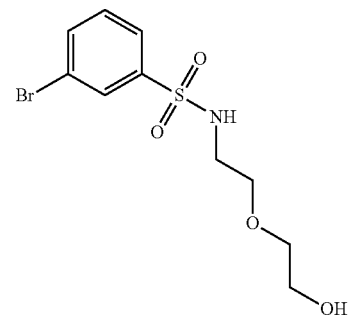

11A

Compound 11A was prepared in analogy to compound 5A of Example 5 by using 2-(2-aminoethoxy)ethanol instead of pyrrolidin-3-ol. MS: m/z=324 (M+H)⁺.

Example 12

2-Amino-8-[3-(6-hydroxyhexylsulfamoyl)phenyl]-N,N-dipropyl-3H-1-benzazepine-4-carboxamide

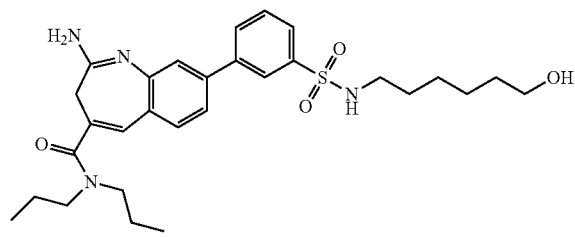 [SMILES: CCCN(CCC)C(=O)C1=Cc2ccc(-c3cccc(S(=O)(=O)NCCCCCCO)c3)cc2N=C(N)C1]

The title compound was prepared in two steps in analogy to Example 4 by using 3-bromo-N-(6-hydroxyhexyl)benzenesulfonamide (Compound 12A) instead of 5-bromopyridine-3-sulfonamide. Example 12 was obtained as a light yellow solid (15 mg). $^1$H NMR (CD$_3$OD, 400 MHz): δ ppm=8.55 (br. s., 1H), 8.15 (s, 1H), 7.83-8.02 (m, 2H), 7.61-7.76 (m, 1H), 7.42-7.58 (m, 2H), 6.98 (s, 1H), 3.35-3.65 (m, 8H), 2.92 (t, J=6.9 Hz, 2H), 1.56-1.85 (m, 4H), 1.21-1.55 (m, 8H), 0.50-1.14 (m, 6H). MS: m/z=541 (M+H)$^+$.

Preparation of 3-bromo-N-(6-hydroxyhexyl)benzenesulfonamide (Compound 12A)

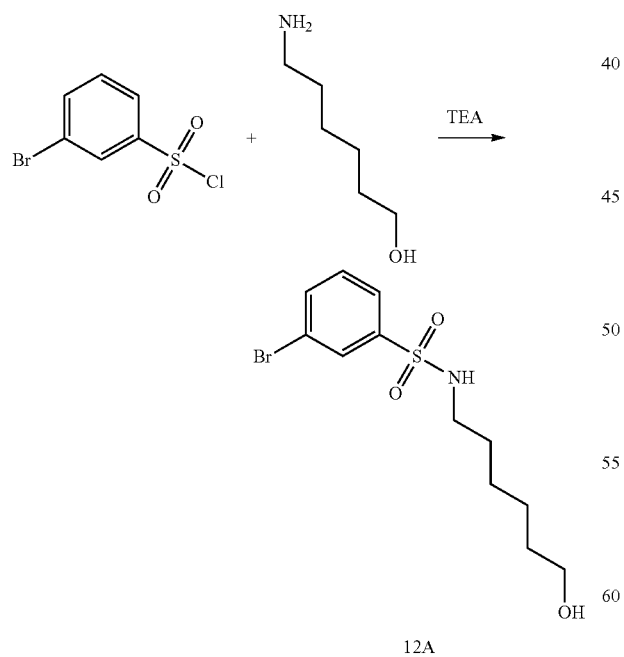

Compound 12A was prepared in analogy to compound 5A of Example 5 by using 6-aminohexan-1-ol instead of pyrrolidin-3-ol. MS: m/z=336 (M+H)$^+$.

Example 13

2-Amino-8-[3-[(4-hydroxy-1-piperidyl)sulfonyl]phenyl]-N,N-dipropyl-3H-1-benzazepine-4-carboxamide

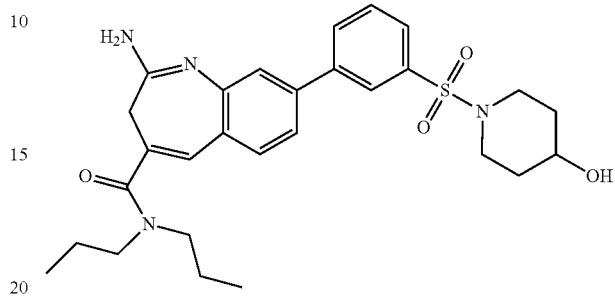

The title compound was prepared in two steps in analogy to Example 4 by using 1-(3-bromophenyl)sulfonylpiperidin-4-ol (Compound 13A) instead of 5-bromopyridine-3-sulfonamide. Example 13 was obtained as a light yellow solid (17 mg). $^1$H NMR (CD$_3$OD, 400 MHz): δ ppm=7.98-8.12 (m, 2H), 7.84-7.92 (m, 1H), 7.62-7.82 (m, 4H), 7.09 (s, 1H), 3.68 (tt, J=7.8, 3.6 Hz, 1H), 3.36-3.58 (m, 8H), 2.75-3.01 (m, 2H), 1.91 (ddd, J=9.8, 6.7, 3.4 Hz, 2H), 1.50-1.81 (m, 6H), 0.97 (br. s, 6H). MS: m/z=525 (M+H)$^+$.

Preparation of 1-(3-bromophenyl)sulfonylpiperidin-4-ol (Compound 13A)

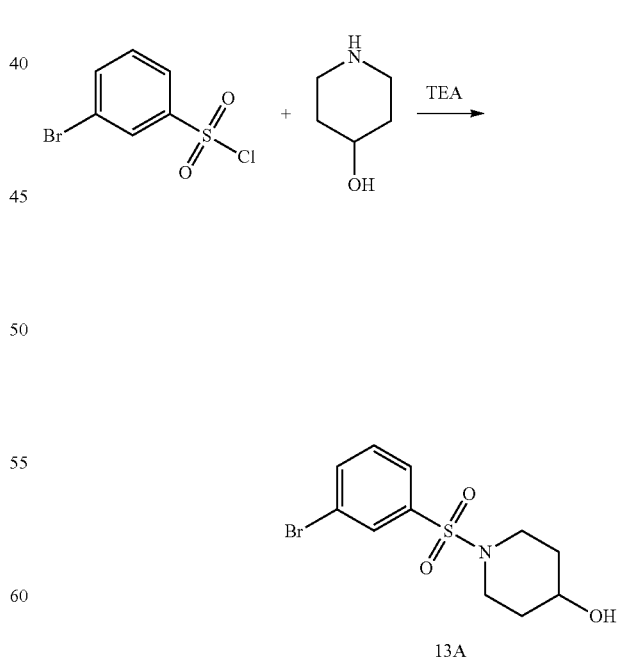

Compound 13A was prepared in analogy to compound 5A of Example 5 by using piperidin-4-ol instead of pyrrolidin-3-ol. MS: m/z=320 (M+H)$^+$.

Example 14

2-Amino-8-[3-[(3R)-3-hydroxypyrrolidin-1-yl]sulfonyl-5-(trifluoromethyl)phenyl]-N,N-dipropyl-3H-1-benzazepine-4-carboxamide

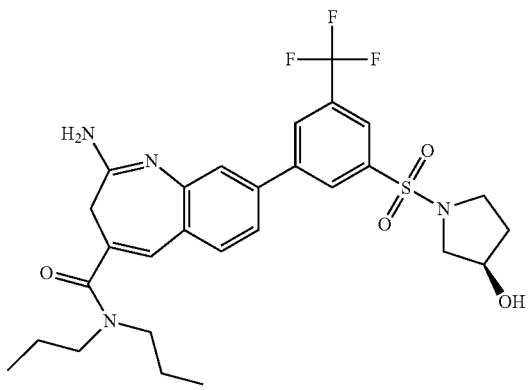 [SMILES: CCCN(CCC)C(=O)C1=Cc2ccc(-c3cc(C(F)(F)F)cc(S(=O)(=O)N4CC[C@@H](O)C4)c3)cc2N=C(N)C1]

The title compound was prepared in two steps in analogy to Example 4 by using tert-butyl N-[4-(dipropylcarbamoyl)-8-(4,4,5,5-tetramethyl-1,3,2-dioxaborolan-2-yl)-3H-1-benzazepin-2-yl]carbamate and (3R)-1-[3-bromo-5-(trifluoromethyl)phenyl]sulfonylpyrrolidin-3-ol (Compound 14A) instead of 5-bromopyridine-3-sulfonamide. Example 14 was obtained as a light yellow solid (20 mg). $^1$H NMR (CD$_3$OD, 400 MHz): δ ppm=8.37 (s, 1H), 8.28 (s, 1H), 8.13 (s, 1H), 7.56-7.80 (m, 3H), 7.07 (s, 1H), 4.27-4.41 (m, 1H), 3.36-3.59 (m, 8H), 1.61-2.15 (m, 8H), 0.98 (br. s., 6H). MS: m/z=579 (M+H)$^+$.

Preparation of (3R)-1-[3-bromo-5-(trifluoromethyl)phenyl]sulfonylpyrrolidin-3-ol (Compound 14A)

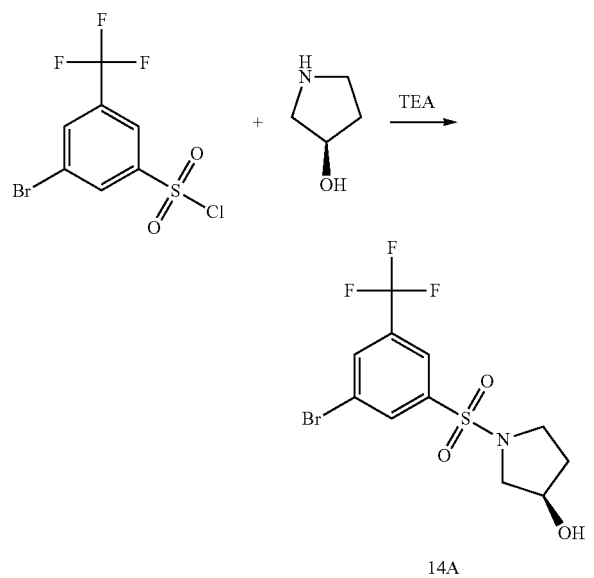

Compound 14A was prepared in analogy to compound 5A of Example 5 by using (3R)-pyrrolidin-3-ol and 3-bromo-5-(trifluoromethyl)benzenesulfonyl chloride instead of pyrrolidin-3-ol and 3-bromo-benzenesulfonyl chloride. MS: m/z=374 (M+H)$^+$.

Example 15

2-Amino-8-[3-[(3R)-3-hydroxypyrrolidin-1-yl]sulfonyl-4-methoxy-phenyl]-N,N-dipropyl-3H-1-benzazepine-4-carboxamide

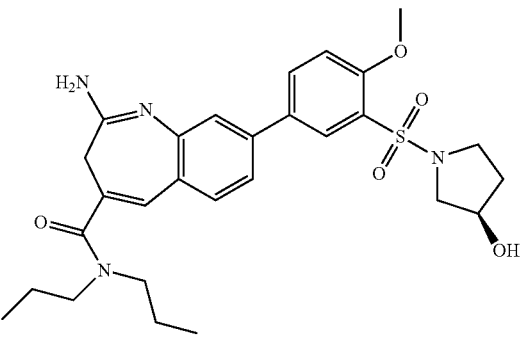 [SMILES: CCCN(CCC)C(=O)C1=Cc2ccc(-c3ccc(OC)c(S(=O)(=O)N4CC[C@@H](O)C4)c3)cc2N=C(N)C1]

The title compound was prepared in two steps in analogy to Example 4 by using (3R)-1-(5-bromo-2-methoxy-phenyl)sulfonylpyrrolidin-3-ol (Compound 15A) instead of 5-bromopyridine-3-sulfonamide. Example 15 was obtained as a light yellow solid (9 mg). $^1$H NMR (CD$_3$OD, 400 MHz): δ ppm=8.19 (d, J=2.3 Hz, 1H), 7.95 (dd, J=8.7, 2.4 Hz, 1H), 7.49-7.60 (m, 3H), 7.35 (d, J=8.8 Hz, 1H), 7.00 (s, 1H), 4.34-4.46 (m, 1H), 3.94-4.12 (m, 3H), 3.36-3.66 (m, 8H), 3.17-3.31 (m, 2H), 1.82-2.10 (m, 2H), 1.71 (dq, J=14.9, 7.5 Hz, 4H), 0.96 (br. s., 6H). MS: m/z=541 (M+H)$^+$.

Preparation of (3R)-1-(5-bromo-2-methoxy-phenyl)sulfonylpyrrolidin-3-ol (Compound 15A)

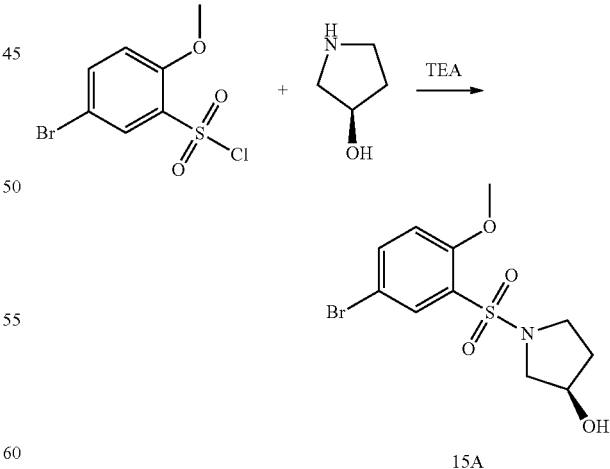

Compound 15A was prepared in analogy to compound 5A of Example 5 by using (3R)-pyrrolidin-3-ol and 5-bromo-2-methoxy-benzenesulfonyl chloride instead of pyrrolidin-3-ol and 3-bromo-benzenesulfonyl chloride. MS: m/z=336 (M+H)$^+$.

Example 16

2-Amino-8-[3-[3-(hydroxymethyl)azetidin-1-yl]sulfonylphenyl]-N,N-dipropyl-3H-1-benzazepine-4-carboxamide

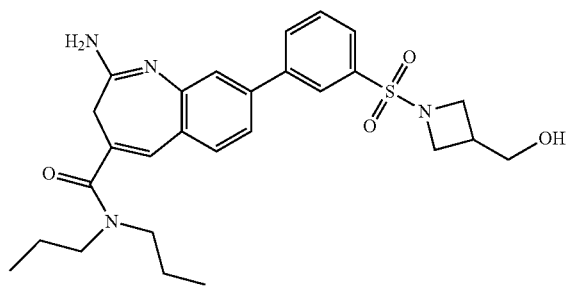

The title compound was prepared in two steps in analogy to Example 4 by using [1-(3-bromophenyl)sulfonylazetidin-3-yl]methanol (Compound 16A) instead of 5-bromopyridine-3-sulfonamide. Example 16 was obtained as a light yellow solid (10 mg). ¹H NMR (CD$_3$OD, 400 MHz): δ ppm=8.02-8.18 (m, 2H), 7.78-7.98 (m, 2H), 7.60-7.76 (m, 3H), 7.07 (s, 1H), 3.77-3.97 (m, 3H), 3.36-3.69 (m, 8H), 2.42-2.74 (m, 2H), 1.72 (m, 4H), 0.96 (br. s., 6H). MS: m/z=511 (M+H)$^+$.

Preparation of [1-(3-bromophenyl)sulfonylazetidin-3-yl]methanol (Compound 16A)

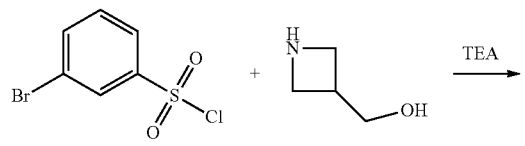

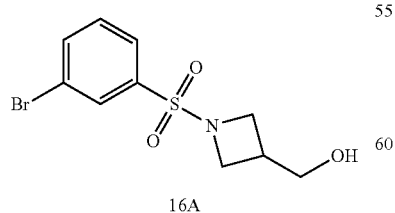

16A

Compound 16A was prepared in analogy to compound 5A of Example 5 by using azetidin-3-ylmethanol instead of pyrrolidin-3-ol. MS: m/z=306 (M+H)$^+$.

Example 17

2-Amino-8-[3-[[(3R)-3-hydroxy-1-piperidyl]sulfonyl]phenyl]-N,N-dipropyl-3H-1-benzazepine-4-carboxamide

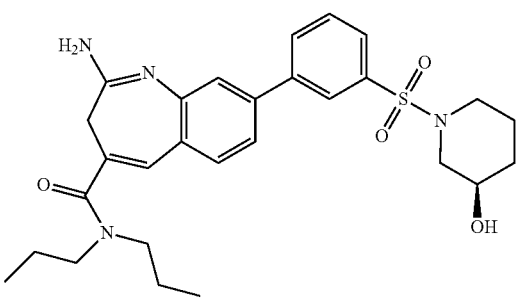 [SMILES: CCCN(CCC)C(=O)C1=Cc2ccc(-c3cccc(S(=O)(=O)N4CCC[C@@H](O)C4)c3)cc2N=C(N)C1]

The title compound was prepared in two steps in analogy to Example 4 by using (3R)-1-(3-bromophenyl)sulfonylpiperidin-3-ol (Compound 17A) instead of 5-bromopyridine-3-sulfonamide. Example 17 was obtained as a light yellow solid (12 mg). ¹H NMR (CD$_3$OD, 400 MHz): δ ppm=7.97-8.09 (m, 2H), 7.70-7.89 (m, 2H), 7.45-7.64 (m, 3H), 6.93-7.06 (m, 1H), 3.66-3.83 (m, 1H), 3.36-3.64 (m, 8H), 2.52-2.63 (m, 1H), 2.43 (dd, J=11.0, 8.8 Hz, 1H), 1.49-1.94 (m, 7H), 1.17-1.37 (m, 1H), 0.96 (br. s., 6H). MS: m/z=525 (M+H)$^+$.

Preparation of (3R)-1-(3-bromophenyl)sulfonylpiperidin-3-ol (Compound 17A)

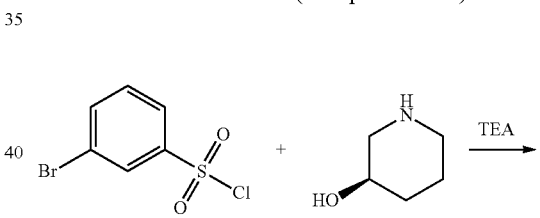

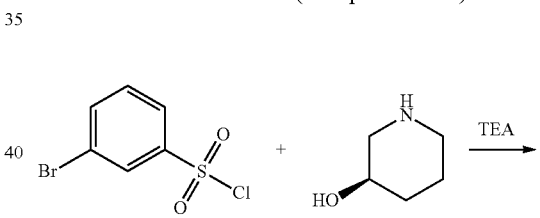

17A

Compound 17A was prepared in analogy to compound 5A of Example 5 by using (3R)-piperidin-3-ol instead of pyrrolidin-3-ol. MS: m/z=320 (M+H)$^+$.

Example 18

2-Amino-8-[3-[[(3S)-3-hydroxy-1-piperidyl]sulfonyl]phenyl]-N,N-dipropyl-3H-1-benzazepine-4-carboxamide

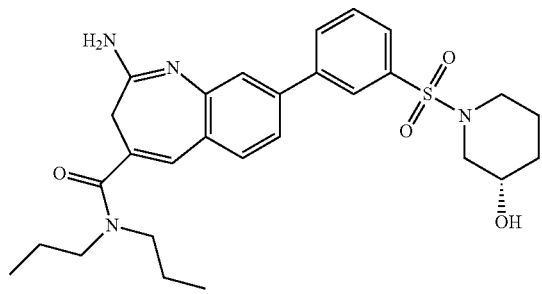 [SMILES: CCCN(CCC)C(=O)C1=Cc2ccc(-c3cccc(S(=O)(=O)N4CCC[C@H](O)C4)c3)cc2N=C(N)C1]

The title compound was prepared in two steps in analogy to Example 4 by using (3S)-1-(3-bromophenyl)sulfonylpiperidin-3-ol (Compound 18A) instead of 5-bromopyridine-3-sulfonamide. Example 18 was obtained as a light yellow solid (5 mg). $^1$H NMR (CD$_3$OD, 400 MHz): δ ppm=7.97-8.13 (m, 2H), 7.72-7.89 (m, 2H), 7.53-7.70 (m, 3H), 7.06 (s, 1H), 3.68-3.79 (m, 1H), 3.37-3.65 (m, 8H), 2.51-2.71 (m, 1H), 2.43 (dd, J=11.0, 8.8 Hz, 1H), 1.51-1.94 (m, 7H), 1.17-1.39 (m, 1H), 0.96 (br. s., 6H). MS: m/z=525 (M+H)$^+$.

Preparation of (3S)-1-(3-bromophenyl)sulfonylpiperidin-3-ol (Compound 18A)

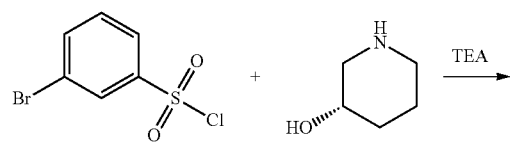

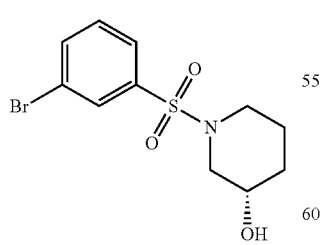

18A

Compound 18A was prepared in analogy to compound 5A of Example 5 by (3S)-piperidin-3-ol instead of pyrrolidin-3-ol. MS: m/z=320 (M+H)$^+$.

Example 19

2-Amino-8-[3-[(3R)-3-hydroxypyrrolidin-1-yl]sulfonyl-2-methyl-phenyl]-N,N-dipropyl-3H-1-benzazepine-4-carboxamide

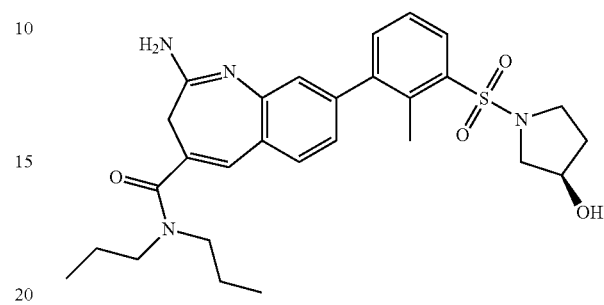

The title compound was prepared in two steps in analogy to Example 4 by using (3R)-1-(3-bromo-2-methyl-phenyl)sulfonylpyrrolidin-3-ol (Compound 19A) instead of 5-bromopyridine-3-sulfonamide. Example 19 was obtained as a light yellow solid (12 mg). $^1$H NMR (CD$_3$OD, 400 MHz): δ ppm=8.02 (dd, J=7.7, 1.4 Hz, 1H), 7.39-7.55 (m, 3H), 7.11-7.22 (m, 2H), 6.99 (s, 1H), 4.43-4.55 (m, 1H), 3.42-3.58 (m, 6H), 3.20-3.22 (m, 5H), 2.55 (s, 3H), 1.91-2.19 (m, 2H), 1.72 (dq, J=14.9, 7.3 Hz, 3H), 0.97 (br. s., 6H). MS: m/z=525 (M+H)$^+$.

Preparation of (3R)-1-(3-bromo-2-methyl-phenyl)sulfonylpyrrolidin-3-ol (Compound 19A)

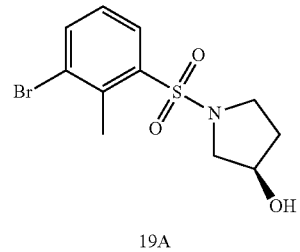

19A

Compound 19A was prepared in analogy to compound 5A of Example 5 by (3R)-piperidin-3-ol and 3-bromo-2-methyl-benzenesulfonyl chloride instead of pyrrolidin-3-ol and 3-bromo-benzenesulfonyl chloride. MS: m/z=320 (M+H)$^+$.

Example 20

2-Amino-8-(5-piperazin-1-ylsulfonyl-3-pyridyl)-N,N-dipropyl-3H-1-benzazepine-4-carboxamide

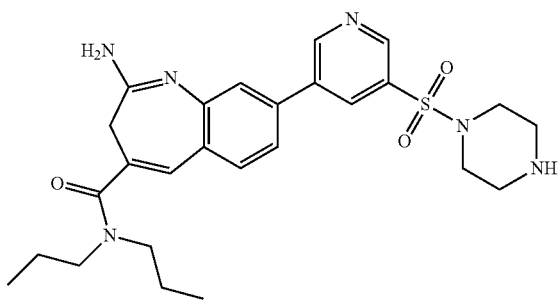 [SMILES: CCCN(CCC)C(=O)C1=Cc2ccc(-c3cncc(S(=O)(=O)N4CCNCC4)c3)cc2N=C(N)C1]

The title compound was prepared in two steps in analogy to Example 4 by using tert-butyl 4-[(5-bromo-3-pyridyl)sulfonyl]piperazine-1-carboxylate (Compound 20A) instead of 5-bromopyridine-3-sulfonamide. Example 20 was obtained as a brown solid (22.9 mg). $^1$H NMR (CD$_3$CN, 400 MHz) δ ppm=9.16 (s, 1H), 8.89 (s, 1H), 8.27 (s, 1H), 7.48-7.36 (m, 3H), 6.83 (s, 1H), 5.72 (s, 2H), 3.41-3.37 (m, 4H), 3.01-2.98 (m, 4H), 2.85-2.83 (m, 4H), 2.78 (s, 2H), 1.67-1.59 (m. 4H), 0.89 (s, 6H). MS: m/z=511 (M+H)$^+$.

Preparation of tert-butyl 4-[(5-bromo-3-pyridyl)sulfonyl]piperazine-1-carboxylate (Compound 20A)

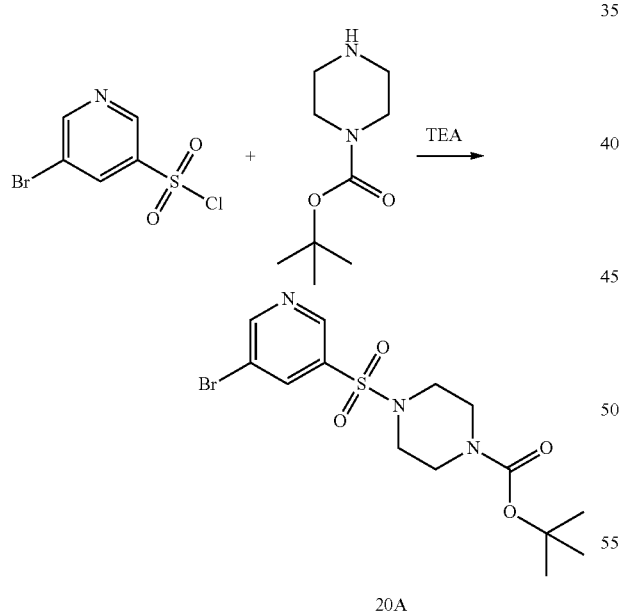

20A

To a stirred solution of 1-boc-piperazine (219 mg, 1.17 mmol) in DCM (3 mL) was added successively TEA (157 mg, 1.56 mmol) and 5-bromopyridine-3-sulfonyl chloride (200 mg, 0.78 mmol) under N$_2$ atmosphere at 0° C. The reaction was stirred at 25° C. for 1 h. Water (3 mL) was added and the mixture was extracted with DCM (3 mL). The separated organic layer was washed with 1 M hydrochloric acid, saturated NaHCO$_3$ solution, dried over Na$_2$SO$_4$ and concentrated to give tert-butyl 4-[(5-bromo-3-pyridyl)sulfonyl]piperazine-1-carboxylate (compound 20A, 250 mg) which can be used in the next step without any purification. MS: m/z=406 (M+H)$^+$.

Example 21

2-Amino-8-(3-piperazin-1-ylsulfonylphenyl)-N,N-dipropyl-3H-1-benzazepine-4-carboxamide

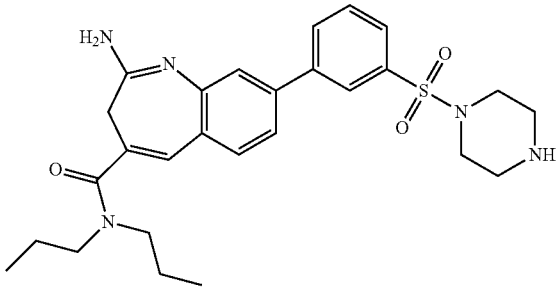 [SMILES: CCCN(CCC)C(=O)C1=Cc2ccc(-c3cccc(S(=O)(=O)N4CCNCC4)c3)cc2N=C(N)C1]

The title compound was prepared in 2 steps in analogy to Example 4 by using tert-butyl 4-(3-bromophenyl)sulfonylpiperazine-1-carboxylate (Compound 21A) instead of 5-bromopyridine-3-sulfonamide. Example 21 was obtained as a light yellow solid (10 mg). $^1$H NMR (CDCl3, 400 MHz) δ ppm=8.04 (s, 1H), 7.89 (d, J=7.78 Hz, 1H), 7.74 (d, J=7.91 Hz, 1H), 7.59-7.66 (m, 1H), 7.52 (d, J=1.63 Hz, 1H), 7.37-7.43 (m, 1H), 7.31 (dd, J=8.09, 1.82 Hz, 1H), 6.86 (s, 1H), 3.49 (br. s., 4H), 3.01-3.10 (m, 4H), 2.91-2.99 (m, 4H), 2.84 (s, 2H), 1.69 (dq, J=15.00, 7.38 Hz, 4H), 0.96 (t, J=7.28 Hz, 6H). MS: m/z=510 (M+H)$^+$.

Preparation of tert-butyl 4-(3-bromophenyl)sulfonylpiperazine-1-carboxylate (Compound 21A)

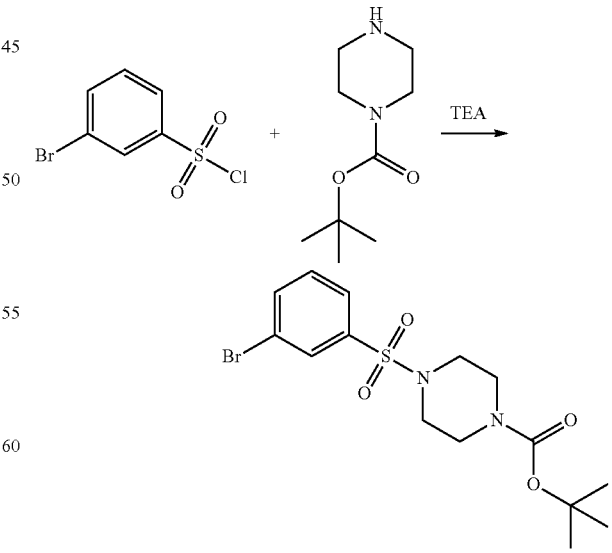

21A

Compound 21A was prepared in analogy to compound 20A of Example 20 by using 3-bromobenzenesulfonyl chloride instead of 5-bromopyridine-3-sulfonyl chloride. MS: m/z=405 (M+H)⁺.

Example 22

2-Amino-8-[5-(3-aminopyrrolidin-1-yl)sulfonyl-3-pyridyl]-N,N-dipropyl-3H-1-benzazepine-4-carboxamide

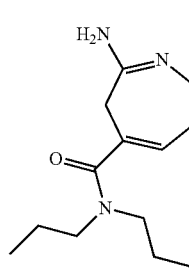

The title compound was prepared in two steps in analogy to Example 4 by using tert-butyl N-[1-[(5-bromo-3-pyridyl)sulfonyl]pyrrolidin-3-yl]carbamate (Compound 22A) instead of 5-bromopyridine-3-sulfonamide. Example 22 was obtained as a yellow solid (17 mg). ¹H NMR (CDCl₃, 400 MHz) δ ppm=8.95-9.19 (m, 2H), 8.37 (s, 1H), 7.49-7.57 (m, 1H), 7.39-7.49 (m, 1H), 7.30-7.37 (m, 1H), 6.82-6.91 (m, 1H), 4.93-5.40 (m, 2H), 3.23-3.72 (m, 8H), 2.98-3.10 (m, 1H), 2.83 (s, 2H), 1.99-2.13 (m, 1H), 1.68-1.90 (m, 5H), 0.96 (t, J=7.16 Hz, 6H). MS: m/z=511 (M+H)⁺.

Preparation of tert-butyl N-[1-[(5-bromo-3-pyridyl)sulfonyl]pyrrolidin-3-yl]carbamate (Compound 22A)

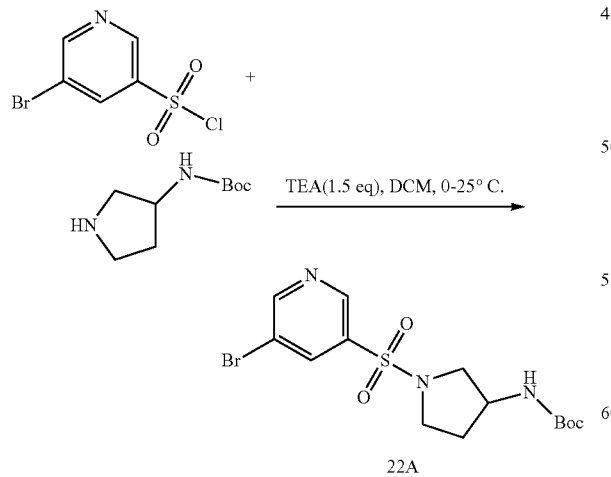

Compound 22A was prepared in analogy to compound 20A of Example 20 by using tert-butyl pyrrolidin-3-ylcarbamate instead of 1-boc-piperazine. MS: m/z=406 (M+H)⁺.

Example 23

2-Amino-8-[3-[(3R)-3-hydroxypyrrolidin-1-yl]sulfonyl-5-methyl-phenyl]-N,N-dipropyl-3H-1-benzazepine-4-carboxamide

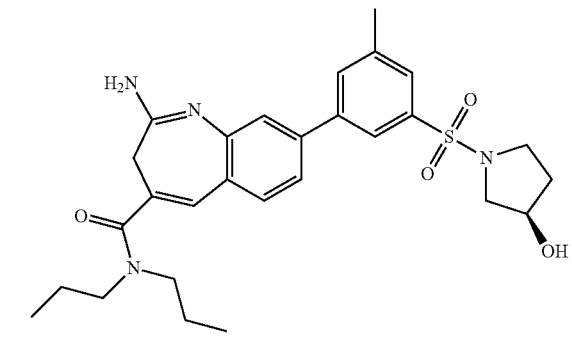 [SMILES: CCCN(CCC)C(=O)C1=Cc2ccc(-c3cc(C)cc(S(=O)(=O)N4CC[C@@H](O)C4)c3)cc2N=C(N)C1]

The title compound was prepared in two steps in analogy to Example 4 by using (3R)-1-(3-bromo-2-methyl-phenyl)sulfonylpyrrolidin-3-ol (Compound 23A) instead of 5-bromopyridine-3-sulfonamide. Example 23 was obtained as a light yellow solid (12 mg). ¹H NMR (CD₃OD, 400 MHz): δ ppm=7.92 (s, 1H), 7.84 (s, 1H), 7.62-7.69 (m, 4H), 7.07 (s, 1H), 4.43-4.55 (m, 1H), 3.40-3.58 (m, 6H), 3.20-3.22 (m, 5H), 2.55 (s, 3H), 1.91-1.98 (m, 2H), 1.72 (m, 3H), 0.97 (br. s., 6H). MS: m/z=525 (M+H)⁺.

Preparation of (3R)-1-(3-bromo-5-methyl-phenyl)sulfonylpyrrolidin-3-ol (Compound 23A)

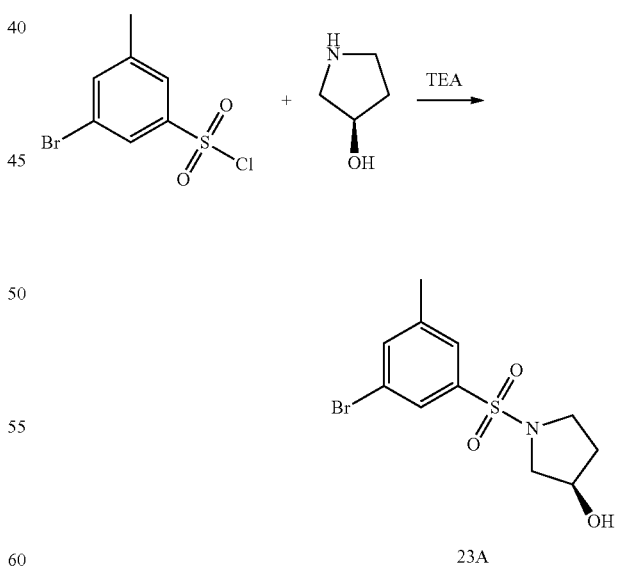

Compound 23A was prepared in analogy to compound 5A of Example 5 by using (3R)-piperidin-3-ol and 3-bromo-5-methyl-benzenesulfonyl chloride instead of pyrrolidin-3-ol and 3-bromo-benzenesulfonyl chloride. MS: m/z=320 (M+H)⁺.

We claim:
1. A compound of the formula

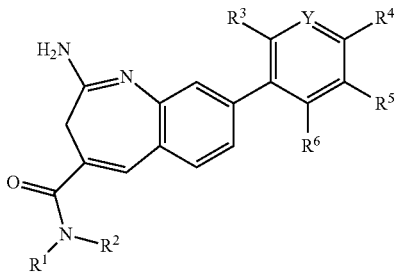

wherein
R$^1$ and R$^2$ are the same or different and are selected from the group consisting of C$_{1-7}$-alkyl, hydroxy-C$_{2-7}$-alkyl, C$_{2-7}$-alkenyl and C$_{3-7}$-alkynyl;
R$^3$ is hydrogen or C$_{1-7}$-alkyl;
R$^6$ is hydrogen or C$_{1-7}$-alkyl;
one of R$^4$ and R$^5$ is selected from the group consisting of hydrogen, C$_{1-7}$-alkyl, halogen-C$_{1-7}$-alkyl and C$_{1-7}$-alkoxy,
and the other one of R$^4$ and R$^5$ is

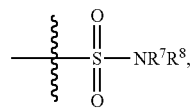

wherein R$^7$ and R$^8$ are the same or different and are selected from the group consisting of hydrogen, C$_{1-7}$-alkyl, halogen-C$_{1-7}$-alkyl, hydroxy-C$_{1-7}$-alkyl, hydroxy-C$_{1-7}$-alkoxy-C$_{1-7}$-alkyl, amino-C$_{1-7}$-alkyl, C$_{1-7}$-alkyl-amino-C$_{1-7}$-alkyl, amino-C$_{1-7}$-alkoxy-C$_{1-7}$-alkyl, C$_{1-7}$-alkyl-amino-C$_{1-7}$-alkoxy-C$_{1-7}$-alkyl, amino-C$_{1-7}$-alkyl-carbonyl and C$_{1-7}$-alkyl-amino-C$_{1-7}$-alkyl-carbonyl, or
R$^7$ and R$^8$ together with the nitrogen atom they are attached to form a 4- to 6-membered heterocycle which is unsubstituted or substituted with a group selected from the group consisting of amino, C$_{1-7}$-alkyl-amino, hydroxy and hydroxy-C$_{1-7}$-alkyl and which may contain an additional N—R$^{10}$ group, wherein R$^{10}$ is selected from the group consisting of hydrogen, amino-C$_{1-7}$-alkyl and C$_{1-7}$-alkyl-amino-C$_{1-7}$-alkyl;
Y is N or CR$^9$,
wherein R$^9$ is selected from the group consisting of hydrogen, C$_{1-7}$-alkyl and halogen-C$_{1-7}$-alkyl;
or a pharmaceutically acceptable salt thereof.
2. The compound of formula I according to claim 1 wherein R$^1$ is C$_{1-7}$-alkyl.
3. The compound of formula I according to claim 2 wherein R$^1$ is propyl.
4. The compound of formula I according to claim 1 wherein R$^2$ is C$_{1-7}$-alkyl.
5. The compound of formula I according to claim 1 wherein R$^1$ and R$^2$ are independently C$_{1-7}$-alkyl.
6. The compound of formula I according to claim 1 wherein R$^3$ and R$^6$ are hydrogen.
7. The compound of formula I according claim 1, wherein R$^4$ is selected from the group consisting of hydrogen, C$_{1-7}$-alkyl, halogen-C$_{1-7}$-alkyl and C$_{1-7}$-alkoxy; and,
R$^5$ is —S(O)$_2$NR$^7$R$^8$,
wherein R$^7$ and R$^8$ are the same or different and are selected from the group consisting of hydrogen, C$_{1-7}$-alkyl, halogen-C$_{1-7}$-alkyl, hydroxy-C$_{1-7}$-alkyl, hydroxy-C$_{1-7}$-alkoxy-C$_{1-7}$-alkyl, amino-C$_{1-7}$-alkyl, C$_{1-7}$-alkyl-amino-C$_{1-7}$-alkyl, amino-C$_{1-7}$-alkoxy-C$_{1-7}$-alkyl, C$_{1-7}$-alkyl-amino-C$_{1-7}$-alkoxy-C$_{1-7}$-alkyl, amino-C$_{1-7}$-alkyl-carbonyl and C$_{1-7}$-alkyl-amino-C$_{1-7}$-alkyl-carbonyl, or
R$^7$ and R$^8$ together with the nitrogen atom they are attached to form a 4- to 6-membered heterocycle which is unsubstituted or substituted with a group selected from the group consisting of amino, C$_{1-7}$-alkyl-amino, hydroxy and hydroxy-C$_{1-7}$-alkyl and which may contain an additional N—R$^{10}$ group, wherein R$^{10}$ is selected from the group consisting of hydrogen, amino-C$_{1-7}$-alkyl and C$_{1-7}$-alkyl-amino-C$_{1-7}$-alkyl.
8. The compound of formula I according to claim 7, wherein R$^7$ and R$^8$ are the same or different and are selected from the group consisting of hydrogen, C$_{1-7}$-alkyl, halogen-C$_{1-7}$-alkyl, hydroxy-C$_{1-7}$-alkyl, hydroxy-C$_{1-7}$-alkoxy-C$_{1-7}$-alkyl, amino-C$_{1-7}$-alkyl, C$_{1-7}$-alkyl-amino-C$_{1-7}$-alkyl, amino-C$_{1-7}$-alkoxy-C$_{1-7}$-alkyl, C$_{1-7}$-alkyl-amino-C$_{1-7}$-alkoxy-C$_{1-7}$-alkyl, amino-C$_{1-7}$-alkyl-carbonyl and C$_{1-7}$-alkyl-amino-C$_{1-7}$-alkyl-carbonyl.
9. The compound of formula I according to claim 8, wherein R$^7$ and R$^8$ are the same or different and are selected from the group consisting of hydrogen, C$_{1-7}$-alkyl, hydroxy-C$_{1-7}$-alkyl and hydroxy-C$_{1-7}$-alkoxy-C$_{1-7}$-alkyl.
10. The compound of formula I according to claim 7, wherein R$^7$ and R$^8$ together with the nitrogen atom they are attached to form a 4- to 6-membered heterocycle which is unsubstituted or substituted with a group selected from the group consisting of amino, C$_{1-7}$-alkyl-amino, hydroxy and hydroxy-C$_{1-7}$-alkyl and which may contain an additional N—R$^{10}$ group, wherein R$^{10}$ is selected from the group consisting of hydrogen, amino-C$_{1-7}$-alkyl and C$_{1-7}$-alkyl-amino-C$_{1-7}$-alkyl.
11. The compound of formula I according to claim 10, wherein R$^7$ and R$^8$ together with the nitrogen atom they are attached to form a 4- to 6-membered heterocycle which is substituted with a group selected from the group consisting of amino, hydroxy and hydroxy-C$_{1-7}$-alkyl.
12. The compound of formula I according to claim 11, wherein Y is N.
13. The compound of formula I according to claim 10, wherein Y is CR$^9$, wherein R$^9$ is selected from the group consisting of hydrogen, C$_{1-7}$-alkyl and halogen-C$_{1-7}$-alkyl.
14. The compound of formula I according to claim 1, selected from the group consisting of:
2-amino-N,N-dipropyl-8-(3-sulfamoylphenyl)-3H-1-benzazepine-4-carboxamide,
2-amino-8-[3-(2-hydroxyethylsulfamoyl)phenyl]-N,N-dipropyl-3H-1-benzazepine-4-carboxamide,
2-amino-N,N-dipropyl-8-(3-pyrrolidin-1-ylsulfonylphenyl)-3H-1-benzazepine-4-carboxamide,
2-amino-N,N-dipropyl-8-(5-sulfamoyl-3-pyridyl)-3H-1-benzazepine-4-carboxamide,
2-amino-8-[3-(3-hydroxypyrrolidin-1-yl)sulfonylphenyl]-N,N-dipropyl-3H-1-benzazepine-4-carboxamide,
2-amino-8-[4-(3-hydroxypyrrolidin-1-yl)sulfonylphenyl]-N,N-dipropyl-3H-1-benzazepine-4-carboxamide,
2-amino-8-[3-[(3R)-3-hydroxypyrrolidin-1-yl]sulfonylphenyl]-N,N-dipropyl-3H-1-benzazepine-4-carboxamide, 2-amino-8-[3-[(3S)-3-hydroxypyrrolidin-1-yl]sulfonyl-phenyl]-N,N-dipropyl-3H-1-benzazepine-4-carboxamide,
2-amino-8-[3-(3-hydroxyazetidin-1-yl)sulfonylphenyl]-N,N-dipropyl-3H-1-benzazepine-4-carboxamide,
2-amino-8-[3-[2-hydroxyethyl(methyl)sulfamoyl]phenyl]-N,N-dipropyl-3H-1-benzazepine-4-carboxamide,
2-amino-8-[3-[2-(2-hydroxyethoxy)ethylsulfamoyl]phenyl]-N,N-dipropyl-3H-1-benzazepine-4-carboxamide,
2-amino-8-[3-(6-hydroxyhexylsulfamoyl)phenyl]-N,N-dipropyl-3H-1-benzazepine-4-carboxamide,
2-amino-8-[3-[(4-hydroxy-1-piperidyl)sulfonyl]phenyl]-N,N-dipropyl-3H-1-benzazepine-4-carboxamide,
2-amino-8-[3-[(3R)-3-hydroxypyrrolidin-1-yl]sulfonyl-5-(trifluoromethyl)phenyl]-N,N-dipropyl-3H-1-benzazepine-4-carboxamide,
2-amino-8-[3-[(3R)-3-hydroxypyrrolidin-1-yl]sulfonyl-4-methoxy-phenyl]-N,N-dipropyl-3H-1-benzazepine-4-carboxamide,
2-amino-8-[3-[3-(hydroxymethyl)azetidin-1-yl]sulfonyl-phenyl]-N,N-dipropyl-3H-1-benzazepine-4-carboxamide,
2-Amino-8-[3-[[(3R)-3-hydroxy-1-piperidyl]sulfonyl]phenyl]-N,N-dipropyl-3H-1-benzazepine-4-carboxamide,
2-Amino-8-[3-[[(3S)-3-hydroxy-1-piperidyl]sulfonyl]phenyl]-N,N-dipropyl-3H-1-benzazepine-4-carboxamide,
2-Amino-8-[3-[(3R)-3-hydroxypyrrolidin-1-yl]sulfonyl-2-methyl-phenyl]-N,N-dipropyl-3H-1-benzazepine-4-carboxamide,
2-amino-8-(5-piperazin-1-ylsulfonyl-3-pyridyl)-N,N-dipropyl-3H-1-benzazepine-4-carboxamide,
2-amino-8-(3-piperazin-1-ylsulfonylphenyl)-N,N-dipropyl-3H-1-benzazepine-4-carboxamide,
2-amino-8-[5-(3-aminopyrrolidin-1-yl)sulfonyl-3-pyridyl]-N,N-dipropyl-3H-1-benzazepine-4-carboxamide, and,
2-amino-8-[3-[(3R)-3-hydroxypyrrolidin-1-yl]sulfonyl-5-methyl-phenyl]-N,N-dipropyl-3H-1-benzazepine-4-carboxamide,
or a pharmaceutically acceptable salt thereof.

15. The compound of formula I according to claim 1, selected from the group consisting of:
2-amino-N,N-dipropyl-8-(3-pyrrolidin-1-ylsulfonylphenyl)-3H-1-benzazepine-4-carboxamide,
2-amino-8-[3-(3-hydroxypyrrolidin-1-yl)sulfonylphenyl]-N,N-dipropyl-3H-1-benzazepine-4-carboxamide,
2-amino-8-[4-(3-hydroxypyrrolidin-1-yl)sulfonylphenyl]-N,N-dipropyl-3H-1-benzazepine-4-carboxamide,
2-amino-8-[3-[(3R)-3-hydroxypyrrolidin-1-yl]sulfonyl-5-(trifluoromethyl)phenyl]-N,N-dipropyl-3H-1-benzazepine-4-carboxamide,
2-amino-8-[3-[[(3R)-3-hydroxy-1-piperidyl]sulfonyl]phenyl]-N,N-dipropyl-3H-1-benzazepine-4-carboxamide,
2-amino-8-[3-[[(3S)-3-hydroxy-1-piperidyl]sulfonyl]phenyl]-N,N-dipropyl-3H-1-benzazepine-4-carboxamide, and
2-amino-8-(3-piperazin-1-ylsulfonylphenyl)-N,N-dipropyl-3H-1-benzazepine-4-carboxamide,
or a pharmaceutically acceptable salts thereof.

16. A pharmaceutical composition comprising a compound of formula I according to claim 1 and at least one pharmaceutically acceptable excipient, carrier and/or adjuvant.

17. A method for activating Toll-like receptors (TLR) by contacting the receptor with a compound according to claim 1.

18. A method for treating cancer comprising treatment of a patient in need thereof with a therapeutically effective amount of a compound according to claim 1.

19. A process for the manufacture of a compound of formula I as defined in claim 1, which process comprises the steps of:

a) coupling a compound of the formula II

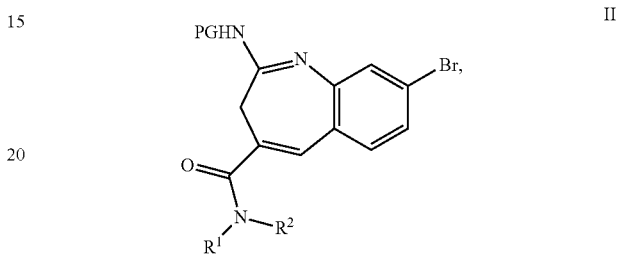

wherein PG is a protecting group, with a compound of the formula III

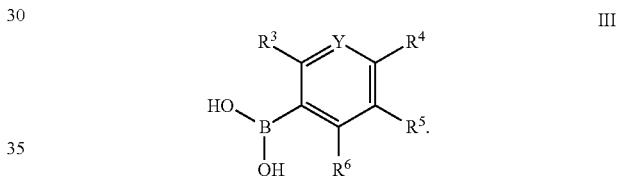

under basic conditions in the presence of a Pd catalyst, and, b) removing the protecting group PG under acidic conditions to afford a compound of the formula I

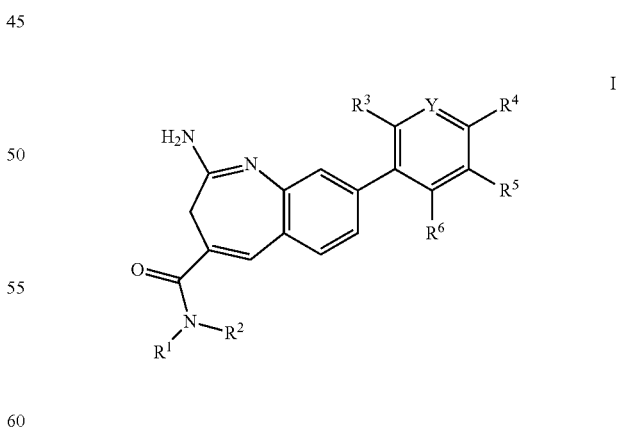

and optionally, converting the compound obtained into a pharmaceutically acceptable salt.

20. A process for the manufacture of a compound of formula I as defined in claim 1, which process comprises the steps of:

a) reacting a compound of the formula II

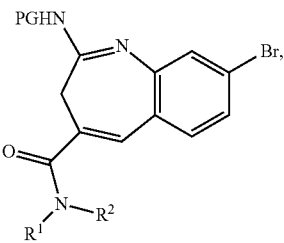

II wherein PG is a protecting group, with bis(pinacolato) diboron under basic conditions in the presence of a Pd catalyst to obtain a boronic ester of the formula V

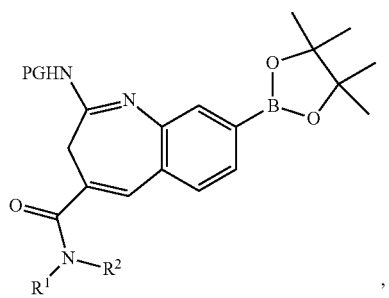

V and (b) coupling the compound V under basic conditions in the presence of a Pd catalyst with a bromide of the formula

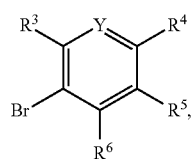

VI and, (c) removing the protecting group PG under acidic conditions to obtain a compound of the formula I

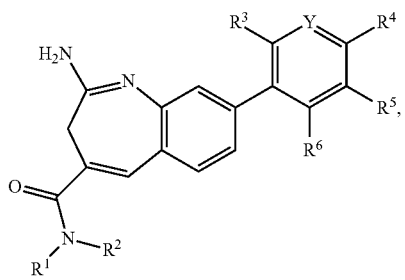

I and optionally converting the compound into a pharmaceutically acceptable salt.

* * * * *